US008486426B2

(12) United States Patent
Maley et al.

(10) Patent No.: US 8,486,426 B2
(45) Date of Patent: Jul. 16, 2013

(54) METHODS AND COMPOSITIONS FOR TREATMENT OF DERMAL CONDITIONS

(75) Inventors: Joseph C. Maley, Sunriver, OR (US); Bruce L. Gibbins, Lake Oswego, OR (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 853 days.

(21) Appl. No.: 10/630,627

(22) Filed: Jul. 29, 2003

(65) Prior Publication Data
US 2004/0096410 A1   May 20, 2004

Related U.S. Application Data

(63) Continuation-in-part of application No. 10/207,936, filed on Jul. 29, 2002, now Pat. No. 6,921,529.

(51) Int. Cl.
*A01N 25/34* (2006.01)

(52) U.S. Cl.
USPC ........... 424/404; 472/447; 472/448; 472/449; 602/55; 602/57; 602/58

(58) Field of Classification Search
None
See application file for complete search history.

(56) References Cited

U.S. PATENT DOCUMENTS

| | | |
|---|---|---|
| 2,396,515 A | 3/1946 | Kreidl et al. |
| 2,934,066 A | 4/1960 | Stowasser et al. |
| 3,092,552 A | 6/1963 | Romans |
| 3,152,094 A | 10/1964 | Erner et al. |
| 3,152,904 A | 10/1964 | Sorensen et al. |
| 3,157,524 A | 11/1964 | Artandi |
| 3,485,658 A | 12/1969 | Iler |
| 3,511,764 A | 5/1970 | Marans et al. |
| 3,624,835 A | 11/1971 | Wyatt |
| 3,645,835 A | 2/1972 | Hodgson |
| 3,647,439 A | 3/1972 | Bass |
| 3,846,236 A | 11/1974 | Updike et al. |
| 3,933,507 A | 1/1976 | Von Konig et al. |
| 3,969,498 A | 7/1976 | Catania et al. |
| 3,996,141 A | 12/1976 | Updike |
| 4,113,658 A | 9/1978 | Geus |
| 4,130,517 A | 12/1978 | Lundberg et al. |
| 4,136,177 A | 1/1979 | Lin et al. |
| 4,136,178 A | 1/1979 | Lin et al. |
| 4,260,677 A | 4/1981 | Winslow et al. |
| 4,306,551 A | 12/1981 | Hymes |
| 4,310,509 A | 1/1982 | Berglund et al. |
| 4,320,201 A | 3/1982 | Berg et al. |
| 4,328,799 A | 5/1982 | LoPiano |
| 4,340,043 A | 7/1982 | Seymour |
| 4,364,929 A | 12/1982 | Sasmor et al. |
| 4,393,048 A | 7/1983 | Mason, Jr. et al. |
| 4,474,571 A | 10/1984 | Lasley |
| 4,483,688 A | 11/1984 | Akiyama |
| 4,529,623 A | 7/1985 | Maggs |
| 4,604,384 A | 8/1986 | Smith et al. |
| 4,608,041 A | 8/1986 | Nielsen |
| 4,612,337 A | 9/1986 | Fox, Jr. et al. |
| 4,624,656 A | 11/1986 | Clark et al. |
| 4,686,211 A | 8/1987 | Hara et al. |
| 4,708,821 A | 11/1987 | Shimokawa et al. |
| 4,721,724 A | 1/1988 | Stettendorf et al. |
| 4,747,847 A | 5/1988 | Magruder et al. |
| 4,782,819 A | 11/1988 | Adair |
| 4,801,291 A | 1/1989 | Loori |
| 4,902,503 A | 2/1990 | Umemura et al. |
| 4,915,694 A | 4/1990 | Yamamoto et al. |
| 4,969,881 A | 11/1990 | Viesturs |
| 5,023,082 A | 6/1991 | Friedman et al. |
| 5,049,139 A | 9/1991 | Gilchrist |
| 5,076,265 A | 12/1991 | Wokalek |
| 5,086,620 A | 2/1992 | Spears |
| 5,091,171 A | 2/1992 | Yu et al. |
| 5,100,668 A | 3/1992 | Edelman et al. |
| 5,128,326 A | 7/1992 | Balazs et al. |
| 5,149,524 A | 9/1992 | Sherba et al. |
| 5,151,271 A | 9/1992 | Otsuka et al. |
| 5,158,772 A | 10/1992 | Davis |
| 5,175,229 A | 12/1992 | Braatz et al. |
| 5,181,914 A | 1/1993 | Zook |
| 5,196,190 A | 3/1993 | Nangia et al. |
| 5,236,421 A | 8/1993 | Becher |
| 5,270,358 A * | 12/1993 | Asmus ........................ 524/55 |
| 5,326,567 A | 7/1994 | Capelli |
| 5,342,528 A | 8/1994 | Adachi et al. |
| 5,354,862 A | 10/1994 | Hsu |
| 5,407,685 A | 4/1995 | Malchesky et al. |

(Continued)

FOREIGN PATENT DOCUMENTS

| | | |
|---|---|---|
| CN | 03820077.5 | 7/2003 |
| DE | 19631421 A1 | 2/1998 |

(Continued)

OTHER PUBLICATIONS

Merriam-Webster Online Dictionary entry for "membrane".*
Supplementary European Search Report for European Application No. 03772113.1 dated Dec. 7, 2006.
Pepe, R.C, Wenninger, J.A., & McEwen, G.N., eds.,Int'l Cosmetic Ingredient Dictionary & Handbook, 9th ed., 2002, vol. 2. p. 177, Cosmetic Toiletry and Fragrance Assoc.
Acticoat RTM, Silver Coated Dressing Marketing Materials. The Westaim Corporation, 1988.
Bharathi, Subramanian et al., "Sol-Gel-Derived Nanocrystalline Gold-Silicate Composite Biosensor," Analytical Communications, 1998, 35: 29-31.
Chase, Grafton D., Pharmaceutical Science by Remington, 14th Edition., Mack Publishing Co., Rheology, Newtonian Flow-Plastic Flow-Pseudoplastic Flow-Dilatant Flow-Methods for Measuring Viscosity-Polymer Solutions-Thixotrophy-Pharmaceutical Applications, 1970, 359-371.

(Continued)

*Primary Examiner* — Hasan Ahmed
(74) *Attorney, Agent, or Firm* — Dority & Manning, P.A.

(57) ABSTRACT

The present invention comprises methods and compositions for the treatment of pathological conditions of the dermis and dermal structures of animals and humans. In particular, the present invention comprises the use of topical delivery vehicles, including hydrogels, which incorporate active agents such as organic acids, for the treatment of dermal conditions.

6 Claims, No Drawings

U.S. PATENT DOCUMENTS

| | | | |
|---|---|---|---|
| 5,429,591 A | 7/1995 | Yamamoto et al. |
| 5,432,077 A | 7/1995 | Farrah |
| 5,447,492 A | 9/1995 | Cartmell et al. |
| 5,453,401 A | 9/1995 | Grivna et al. |
| 5,454,886 A | 10/1995 | Burrell et al. |
| 5,464,610 A | 11/1995 | Hayes, Jr. et al. |
| 5,470,585 A | 11/1995 | Gilchrist |
| 5,503,840 A | 4/1996 | Jacobson et al. |
| 5,508,038 A | 4/1996 | Wang et al. |
| 5,508,417 A | 4/1996 | Osei-Gyimah et al. |
| 5,516,502 A | 5/1996 | Dickerson |
| 5,527,534 A | 6/1996 | Myhling |
| 5,567,495 A | 10/1996 | Modak et al. |
| 5,569,207 A | 10/1996 | Gisselberg et al. |
| 5,593,683 A | 1/1997 | Viegas et al. |
| 5,599,296 A | 2/1997 | Spears |
| 5,603,946 A | 2/1997 | Constantine |
| 5,614,568 A | 3/1997 | Mawatari et al. |
| 5,660,854 A | 8/1997 | Haynes et al. |
| 5,681,579 A | 10/1997 | Freeman |
| 5,683,713 A | 11/1997 | Blank et al. |
| 5,693,624 A | 12/1997 | Hardy et al. |
| 5,695,777 A | 12/1997 | Donovan et al. |
| 5,709,870 A | 1/1998 | Yoshimura et al. |
| 5,725,491 A | 3/1998 | Tipton et al. |
| 5,735,251 A | 4/1998 | Hyodo et al. |
| 5,736,582 A | 4/1998 | Devillez |
| 5,744,151 A | 4/1998 | Capelli |
| 5,753,251 A | 5/1998 | Burrell et al. |
| 5,792,090 A | 8/1998 | Ladin |
| 5,804,213 A | 9/1998 | Rolf |
| 5,820,918 A | 10/1998 | Ronan et al. |
| 5,830,496 A | 11/1998 | Freeman |
| 5,833,665 A | 11/1998 | Bootman et al. |
| 5,840,283 A | 11/1998 | Sorenson et al. |
| 5,853,742 A | 12/1998 | Bartolone et al. |
| 5,855,570 A | 1/1999 | Scherson et al. |
| 5,863,548 A | 1/1999 | Elder |
| 5,863,864 A | 1/1999 | Plath et al. |
| 5,869,073 A | 2/1999 | Sawan et al. |
| 5,908,693 A | 6/1999 | Delgado et al. |
| 5,927,317 A | 7/1999 | Hsia |
| 5,928,174 A | 7/1999 | Gibbins |
| 5,951,458 A | 9/1999 | Hastings et al. |
| 5,961,996 A | 10/1999 | Garson et al. |
| 5,965,204 A | 10/1999 | Sodervall et al. |
| 5,972,317 A | 10/1999 | Sorenson et al. |
| 5,993,790 A | 11/1999 | Strauss |
| 6,000,403 A | 12/1999 | Cantwell |
| 6,004,667 A | 12/1999 | Sakurada et al. |
| 6,011,194 A | 1/2000 | Buglino et al. |
| 6,014,585 A | 1/2000 | Stoddard |
| 6,042,845 A | 3/2000 | Sun et al. |
| 6,051,614 A | 4/2000 | Hirai et al. |
| 6,099,805 A | 8/2000 | Hartlove |
| 6,103,868 A | 8/2000 | Heath et al. |
| 6,110,447 A | 8/2000 | Ramin et al. |
| 6,113,287 A | 9/2000 | Merz et al. |
| 6,143,794 A | 11/2000 | Chaudhuri et al. |
| 6,159,977 A | 12/2000 | Reeves |
| 6,187,290 B1 | 2/2001 | Gilchrist et al. |
| 6,191,339 B1 | 2/2001 | Gueret |
| 6,201,164 B1 | 3/2001 | Wulff et al. |
| 6,214,360 B1 | 4/2001 | Richter et al. |
| 6,224,622 B1 | 5/2001 | Kotzev |
| 6,231,840 B1 | 5/2001 | Buck |
| 6,235,964 B1 | 5/2001 | Kadash et al. |
| 6,248,342 B1 | 6/2001 | Trogolo et al. |
| 6,264,927 B1 | 7/2001 | Monahan |
| 6,270,811 B1 | 8/2001 | Fregonese |
| 6,316,084 B1 | 11/2001 | Claus et al. |
| 6,326,524 B1 | 12/2001 | Fattman et al. |
| 6,355,858 B1 | 3/2002 | Gibbins |
| 6,468,989 B1 | 10/2002 | Chang et al. |
| 6,471,982 B1 | 10/2002 | Lydon et al. |
| 6,530,895 B1 | 3/2003 | Keirn |
| 6,605,751 B1 | 8/2003 | Gibbins |
| 6,669,981 B2 | 12/2003 | Parsons et al. |
| 6,713,075 B2 * | 3/2004 | Bekele | 424/401 |
| 6,716,895 B1 | 4/2004 | Terry |
| 6,897,349 B2 | 5/2005 | Gibbins et al. |
| 6,921,529 B2 | 7/2005 | Maley |
| 7,129,389 B1 | 10/2006 | Watson |
| 7,160,553 B2 | 1/2007 | Gibbins et al. |
| 7,166,330 B2 | 1/2007 | Takahashi et al. |
| 7,189,410 B1 | 3/2007 | Drohan et al. |
| 7,576,255 B2 | 8/2009 | Gibbins et al. |
| 2001/0026810 A1 | 10/2001 | McGhee et al. |
| 2001/0041188 A1 | 11/2001 | Gibbins |
| 2002/0001604 A1 | 1/2002 | Shigeru et al. |
| 2002/0042587 A1 | 4/2002 | Murdock |
| 2002/0073891 A1 | 6/2002 | Parsons et al. |
| 2002/0082340 A1 | 6/2002 | Hanke et al. |
| 2003/0041188 A1 | 2/2003 | Han et al. |
| 2003/0083610 A1 | 5/2003 | McGrath et al. |
| 2003/0093057 A1 | 5/2003 | Zhang et al. |
| 2003/0186955 A1 | 10/2003 | Vange et al. |
| 2004/0010215 A1 | 1/2004 | Gibbins |
| 2004/0062733 A1* | 4/2004 | Birnbaum | 424/61 |
| 2004/0082925 A1 | 4/2004 | Patel |
| 2004/0108462 A1 | 6/2004 | Besesty et al. |
| 2004/0127025 A1 | 7/2004 | Crocker et al. |
| 2004/0147618 A1 | 7/2004 | Lee et al. |
| 2004/0170545 A1 | 9/2004 | Emanuel |
| 2004/0173056 A1 | 9/2004 | McNally et al. |
| 2004/0180093 A1 | 9/2004 | Burton et al. |
| 2004/0253536 A1 | 12/2004 | Park et al. |
| 2004/0254532 A1 | 12/2004 | Mehier |
| 2005/0008861 A1 | 1/2005 | Yadav et al. |
| 2005/0029121 A1 | 2/2005 | Monzyk et al. |
| 2005/0186135 A1 | 8/2005 | Howes |
| 2005/0265894 A1 | 12/2005 | Monzyk et al. |
| 2006/0276740 A1 | 12/2006 | Bagley |
| 2007/0003603 A1 | 1/2007 | Karandikar et al. |
| 2007/0207335 A1 | 9/2007 | Karandikar et al. |
| 2007/0254044 A1 | 11/2007 | Karandikar et al. |
| 2007/0293800 A1 | 12/2007 | McMaken et al. |
| 2010/0034882 A1 | 2/2010 | Gibbins et al. |

FOREIGN PATENT DOCUMENTS

| | | |
|---|---|---|
| EP | 0 072 251 | 2/1983 |
| EP | 0 297 769 | 1/1989 |
| EP | 0 489 206 | 6/1992 |
| EP | 500387 | 8/1992 |
| EP | 0 508 324 | * 10/1992 |
| EP | 0 707 793 | 4/1996 |
| EP | 0 709 101 | 5/1996 |
| EP | 1245239 A1 | 10/2002 |
| EP | 03772113.1 | 7/2003 |
| GB | 863875 A | 3/1961 |
| GB | 1471013 | 4/1977 |
| GB | 1 554 002 | 10/1979 |
| GB | 2024012 | 1/1980 |
| GB | 2134791 A | 8/1984 |
| JP | 05-271718 A | 10/1993 |
| JP | 6-145060 | 5/1994 |
| JP | 6248549 A | 9/1994 |
| JP | 7097767 A | 4/1995 |
| JP | 11302119 A | 11/1999 |
| JP | 2003529630 A | 10/2003 |
| JP | 2004137615 A | 5/2004 |
| JP | 2004161632 A | 6/2004 |
| WO | WO-84/01721 A1 | 5/1984 |
| WO | WO 88/06894 | 9/1988 |
| WO | WO 90/03810 | 4/1990 |
| WO | WO-96/11572 A1 | 4/1996 |
| WO | WO-98/06260 A1 | 2/1998 |
| WO | WO-98/20719 A1 | 5/1998 |
| WO | WO-99/15101 A2 | 4/1999 |
| WO | WO 99 25395 | 5/1999 |
| WO | WO-9926666 A2 | 6/1999 |
| WO | WO-00/09173 A1 | 2/2000 |
| WO | 00/15202 | 3/2000 |
| WO | WO-01/11955 A2 | 2/2001 |
| WO | WO-01/24839 A1 | 4/2001 |
| WO | WO-01/49258 A2 | 7/2001 |
| WO | WO-0226039 A1 | 4/2002 |

| WO | WO-0243743 A1 | 6/2002 |
| WO | WO-02/061403 A1 | 8/2002 |
| WO | WO-02/076518 A1 | 10/2002 |
| WO | WO-03/002089 A1 | 1/2003 |
| WO | WO-03/080231 A1 | 10/2003 |
| WO | WO-04/001880 A1 | 12/2003 |
| WO | WO-2004/010952 A2 | 2/2004 |
| WO | WO-2004/028255 A1 | 4/2004 |
| WO | WO-2004/056404 A2 | 7/2004 |
| WO | WO-2006/015317 A2 | 2/2006 |
| WO | WO-2006/026026 A2 | 3/2006 |
| WO | WO-2006/034249 A2 | 3/2006 |
| WO | WO-2007/095058 A2 | 8/2007 |
| WO | WO-2007/127236 A2 | 11/2007 |
| WO | WO-2008/131070 A1 | 10/2008 |

OTHER PUBLICATIONS

ConvaTec Corp. Aquacel Ag Product Info from website. [internet citation] Retrieved Dec. 9, 2002 from http://www.convatec.com/en_US/company/pr/index.html.

Cooper, Rose, "A Review of the Evidence for the Use of Topical Antimicrobial Agents in Wound Care," World Wide Wounds, 2004, 1-15.

Deitch, E. et al., "Silver-Nylon: a New Antimicrobial Agent". Antimicrobial Agents and Chemotherapy, 1983, 23(3):356-359.

Deitch, E., et al., Abstract, "Silver-impregnated nylon cloth dressing: in vitro and in vivo evaluation of antimicrobial activity," J. Trauma, 1987, pp. 301-304, vol. 27, No. 3.

FDA Approval Letter to begin OxyGenesis marketing. Sep. 19, 2008.

Feng et al, "Study of the initiation mechanism of the vinyl polymerization with the system persulfate/N,N,N',N'-tetramethylethylenediamine," Makromol. Chem. 1988, 189: 77-83.

Fox, Jr., Charles L., "Silver Sulfadiazine-A New Topical", Arch. Surg., vol. 96, pp. 184-188, 1968.

Gibbins et al., AcryDerm Absorbent Oxygen Dressing Point of Use Evaluation: Summary of Results. Draft. Jul. 17, 2009.

Gibbins, B. and Hopman, L., "A Comparison of a New Anti-Microbial Polyacrylate Absorbent Wound Dressing Containing Silver with the Silver-containing Anti-microbial Film Dressings", Presentation at Clinical Symposium on Wound Care, Oct. 2, 1999.

Gibbins, Bruce, "The Antimicrobial Benefits of Silver and the Relevance of Microlattice Technology," Ostomy Wound Manage. Feb. 2003; Suppl:4-7.

Grier, N., "Silver and Its Compounds," Disinfection, Sterilization, and Preservation, 3rd Edition. Seymour S. Block, ed., Lea & Febiger, Philadelphia, 1983; Chapter 18, pp. 375-389.

Hackh's Chemical Dictionary, 4th Edition, McGraw Hill Book Co., New York, 1969; p. 451.

Handbook of Common Polymers, "Polyvinyl Alcohol Including Insolubilised Fibres," Scott & Roff, Jr., W.J., The Chemical Company, 1971, pp. 72-197.

Jia et al., "Effect of locally released oxygen on wound healing," Presented at 18th Annual Meeting of the Wound Healing Society, San Diego, CA. Apr. 2008.

Junhui He et al, "Facile in situ synthesis of noble metal nanoparticles in porous cellulose fibers," Chemistry of Materials, 2003, 15(23): 4401-4406.

Kapoor, Sudhir, "Preparation, Characterization, and Surface Modification of Silver Particles," Langmuir, 1998, 14 (5):1021-1025.

Mackeen, P., et al., "Silver-Coated Nylon Fiber as an Antibacterial Agent," Antimicrobial Agents and Chemotherapy, 1987, 31(1): 93-99.

Milk Composition & Synthesis Resourse Library, Milk Composition-Minerals [retrieved on Dec. 5, 2010], retrieved from the internet<URL:http://ciasses.ansci.illinois.edu/ansc438/milkcompsynth/milkcomp_minerals.html >.

OxyGenesis Dissolved Oxygen Dressings: Case Review, AcryMed, Inc., Jan. 23, 2010.

Price, William R. et al., "Silver Nitrate Burn Dressing, Treatment of Seventy Burned Persons," American Journal of Surgery, 1966, 112:674-680.

Ratner, Buddy D. et al., ACS Symposium Series, No. 31, The American Chemical Society, Synthetic Hydrogels for Biomedical Applications, pp. 1-36.

Rifai et al., "Facile in Situ Silver Nanoparticle Formation in Insulating Porous Polymer Matrices," Chemistry of Materials 2006; 18(1): 21-25.

Roe, David F., Gibbins, Bruce L., and Ladizinsky, Daniel A., "Topical Dissolved Oxygen Penetrates Skin: Model and Method," J Surg Res. 2010, 159(1):e29-e36.

Russel A. and Hugo, W., "Antimicrobial Activity and Action of Silver," Progress in Medicinal Chemistry, vol. 31, G-.P. Ellis & D.K. Luscombe, ed., Elsevier Science B.V., 1994; pp. 351-370.

Schacht, Etienne H., Hydrogel Drug Delivery Systems, Institute of Organic Chemistry, State University Gent, 1984, pp. 259-278.

Sheehan et al, "Anti-bacterial Silver Coatings on Orthopaedic Metals—An in Vitro and Animal Study," Journal of Bone and Joint Surgery. 2003, 85-B(SUPP_II):141.

Silver, Simon, "Bacterial Silver Resistance: Molecular Biology and Uses and Misuses of Silver Compounds," FEMS Microbiology Reviews, 2003, pp. 341-353.

Topical Delivery Methods, undated reference, retrieved from file on May 11, 2011.

Wang et al., "Directing oleate stabilized nanosized silver colloids into organic phases", Langmuir: the ACS Journal of Surfaces and Colloids. 1998; 14:602-610.

Communication regarding the expiration of opposition period issued on Feb. 10, 2006 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Decision to grant a European Pat. issued on Feb. 24, 2005 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Approval of request for amendments/corrections issued on Feb. 15, 2005 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Reply to communication from the Examining Division filed on Dec. 22, 2004 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Result of Consultation by telephone/in person (with time limit) issued on Nov. 9, 2004 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Request for correction/amendment of the text proposed for grant filed on Oct. 26, 2004 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Communication about intention to grant a European Pat. issued on Jun. 18, 2004 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Reply to communication from the Examining Division filed on Aug. 20, 2003 for European Pat. App. No. 98961733.7 which claims priority to PCT/US98/024272 filed on Jan. 13, 1998, published May 27, 1999 as WO 99/027680 (Applicant—Acrymed; Inventors. B.L. Gibbins).

Communication from the Examining Division issued on May 5, 2003 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Reply to communication from the Examining Division filed on Feb. 5, 2003 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Communication from the Examining Division issued on Aug. 1, 2002 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Reply to communication from the Examining Division filed on May 20, 2002 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Communication from the Examining Division issued Jul. 31, 2001 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
PCT Intl. Search Report issued on Jun. 23, 1999 for PCT/US98/24272, filed on Nov. 13, 1998, published May 27, 1999 as WO 99/027680 (Applicant—Acrymed; Inventors: B.L. Gibbins).
PCT Intl. Preliminary exam report issued on Aug. 8, 2001 for PCT/US98/24272, filed on Nov. 13, 1998, published May 27, 1999 as WO 99/027680 (Applicant—Acrymed; Inventors: B.L. Gibbins).
PCT Written opinion issued on Feb. 18, 2000 for PCT/US98/24272, filed on Nov. 13, 1998, published May 27, 1999 as WO 99/027680 (Applicant—Acrymed; Inventors: B.L. Gibbins).
Issue Notification issued on Jul. 14, 1999 for U.S. Appl. No. 08/971,074, filed Nov. 14, 1997 (Inventor—B.L. Gibbins).
Notice of Allowance issued on Feb. 25, 1999 for U.S. Pat. Appl. No. 08/971,074, filed Nov. 14, 1997 (Inventor—B.L. Gibbins).
Examiner Interview Summary/Amendment issued on Dec. 11, 1998 for U.S. Appl. No. 08/971,074, filed Nov. 14, 1997 (Inventor—B.L. Gibbins).
Response after Non-Final Action filed on Nov. 18, 1998 for U.S. Appl. No. 08/971,074, filed Nov. 14, 1997 (Inventor—B.L. Gibbins).
Non-Final Rejection issued on Aug. 19, 1998 for U.S. Appl. No. 08/971,074, filed Nov. 14, 1997 (Inventor—B.L. Gibbins).
Response to Election / Restriction filed on Jul. 10, 1998 for U.S. Appl. No. 08/971,074, filed Nov. 14, 1997 (Inventor—B.L. Gibbins).
Restriction Requirement issued on May 21, 1998 for U.S. Appl. No. 08/971,074, filed Nov. 14, 1997 (Inventor—B.L. Gibbins).
Issue Notification issued on Mar. 12, 2002 for U.S. Appl. No. 09/191,223, filed Nov. 13, 1998 (Inventor—B.L. Gibbins).
Notice of Allowance issued on Sep. 25, 2001 for U.S. Appl. No. 09/191,223, filed Nov. 13, 1998 (Inventor—B.L. Gibbins).
Notice of Allowance issued on Oct. 3, 2000 for U.S. Appl. No. 09/191,223, filed Nov. 13, 1998 (Inventor—B.L. Gibbins).
Response after Non-Final Action filed on Aug. 11, 2000 for U.S. Appl. No. 09/191,223, filed Nov. 13, 1998 (Inventor—B.L. Gibbins).
Non-Final Rejection issued on Apr. 11, 2000 for U.S. Appl. No. 09/191,223, filed Nov. 13, 1998 (Inventor—B.L. Gibbins).
Response to Election / Restriction filed on Mar. 21, 2000 for U.S. Appl. No. 09/191,223, filed Nov. 13, 1998 (Inventor—B.L. Gibbins).
Restriction Requirement issued on Feb. 22, 2000 for U.S. Appl. No. 09/191,223, filed Nov. 13, 1998 (Inventor—B.L. Gibbins).
Communication regarding the expiry of opposition period issued on Sep. 2, 2009 for EP App. No. 970522.9, which claims priority to Intl. Pat. App. No. PCT/US00/26890, filed 9/29/200, published on Apr. 12, 2001 as WO 01/024839 (Applicant—Acrymed, Inc.).
Decision to grant a European Pat. issued on Oct. 2, 2008 for EP App. No. 970522.9, which claims priority to Intl. Pat. App. No. PCT/US00/26890, filed 9/29/200, published on Apr. 12, 2001 as WO 01/024839 (Applicant—Acrymed, Inc.).
Communication about intention to grant a European Pat. issued on Apr. 10, 2008 for EP App. No. 970522.9, which claims priority to Intl. Pat. App. No. PCT/US00/26890, filed 9/29/200, published on Apr. 12, 2001 as WO 01/024839 (Applicant—Acrymed, Inc.).
Reply to communication from the Examining Division filed on Feb. 26, 2008 for EP App. No. 970522.9, which claims priority to Intl. Pat. App. No. PCT/US00/26890, filed 9/29/200, published on Apr. 12, 2001 as WO 01/024839 (Applicant—Acrymed, Inc.).
Communication from the Examining Division issued on Oct. 18, 2007 for Ep App. No. 970522.9, which claims priority to Intl. Pat. App. No. PCT/US00/26890, filed 9/29/200, published on Apr. 12, 2001 as WO 01/024839 (Applicant—Acrymed, Inc.).
Reply to communication from the Examining Division filed on Dec. 28, 2006 for EP App. No. 970522.9, which claims priority to Intl. Pat. App. No. PCT/US00/26890, filed 9/29/200, published on Apr. 12, 2001 as WO 01/024839 (Applicant—Acrymed, Inc.).
Communication from the Examining Division issued on Sep. 1, 2006 for Ep App. No. 970522.9, which claims priority to Intl. Pat. App. No. PCT/US00/26890, filed 9/29/200, published on Apr. 12, 2001 as WO 01/024839 (Applicant—Acrymed, Inc.).
Reply to communication from the Examining Division filed on Mar. 21, 2005 for EP App. No. 970522.9, which claims priority to Intl. Pat. App. No. PCT/US00/26890, filed 9/29/200, published on Apr. 12, 2001 as WO 01/024839 (Applicant—Acrymed, Inc.).
Communication from the Examining Division issued on Sep. 20, 2004 for EP App. No. 970522.9, which claims priority to Intl. Pat. App. No. PCT/US00/26890, filed 9/29/200, published on Apr. 12, 2001 as WO 01/024839 (Applicant—Acrymed, Inc.).
Reply to communication from the Examining Division filed on Feb. 27, 2003 for EP App. No. 970522.9, which claims priority to Intl. Pat. App. No. PCT/US00/26890, filed 9/29/200, published on Apr. 12, 2001 as WO 01/024839 (Applicant—Acrymed, Inc.).
Communication from the Examining Division issued on Aug. 21, 2002 for EP App. No. 970522.9, which claims priority to Intl. Pat. App. No. PCT/US00/26890, filed 9/29/200, published on Apr. 12, 2001 as WO 01/024839 (Applicant—Acrymed, Inc.).
PCT Intl. Search Report issued on Feb. 5, 2001 for PCT/US00/26890, filed on Sep. 29, 2000, published Apr. 12, 2001 as WO 01/24839 (Applicant—Acrymed; Inventors: Gibbins).
PCT Written Opinion issued on Jul. 23, 2001 for PCT/US00/26890, filed on Sep. 29, 2000, published Apr. 12, 2001 as WO 01/24839 (Applicant—Acrymed; Inventors: Gibbins).
PCT Intl. Preliminary Examination Report issued on Oct. 17, 2001 for PCT/US00/26890, filed on Sep. 29, 2000, published Apr. 12, 2001 as WO 01/24839 (Applicant—Acrymed; Inventors: Gibbins)
Notice of Allowance issued on Apr. 15, 2003 for U.S. Appl. No. 09/675,892, filed Sep. 29, 2000 (Inventor—B.L. Gibbins).
Amendment/Response After Non-Final Rejection filed on Mar. 21, 2003 for U.S. Appl. No. 09/675,892, filed Sep. 29, 2000 (Inventor—B.L. Gibbins).
Non-Final Rejection issued on Nov. 21, 2002 for U.S. Appl. No. 09/675,892, filed Sep. 29, 2000 (Inventor—B.L. Gibbins).
Amendment After Final filed on Oct. 30, 2002 for U.S. Appl. No. 09/675,892, filed Sep. 29, 2000 (Inventor—B.L. Gibbins).
Final Rejection issued on Jul. 31, 2002 for U.S. Appl. No. 09/675,892, filed Sep. 29, 2000 (Inventor—B.L. Gibbins).
Amendment/Response After Non-Final Rejection filed on Apr. 18, 2002 for U.S. Appl. No. 09/675,892, filed Sep. 29, 2000 (Inventor—B.L. Gibbins).
Non-Final Rejection issued on Jan. 18, 2002 for U.S. Appl. No. 09/675,892, filed Sep. 29, 2000 (Inventor—B.L. Gibbins).
Notice of Allowance issued on Mar. 7, 2005 for U.S. Appl. No. 10/441,275, filed May 19, 2003 (Inventor—B.L. Gibbins).
Notice of Allowance/Examiner Interview Summary Record issued on Jul. 2, 2004 for U.S. Appl. No. 10/441,275, filed May 19, 2003 (Inventor—B.L. Gibbins).
Examiner Interview Summary Record (PTOL—413) issued May 26, 2004 for U.S. Appl. No. 10/441,275, filed May 19, 2003 (Inventor—B.L. Gibbins).
Supplemental Preliminary Amendment filed on Mar. 25, 2004 for U.S. Appl. No. 10/441,275, filed May 19, 2003 (Inventor—B.L. Gibbins).
Preliminary Amendment filed on Dec. 2, 2003 for U.S. Appl. No. 10/441,275, filed May 19, 2003 (Inventor—B.L. Gibbins).
Issue Notification issued on Jul. 29, 2009 for U.S. Appl. No. 10/978,556, filed Nov. 1, 2004 (Inventor—B.L. Gibbins).
Notice of Allowance issued on Apr. 16, 2009 for U.S. Appl. No. 10/978,556, filed Nov. 1, 2004 (Inventor—B.L. Gibbins).
Terminal Disclaimer/Amendment After Final Rejection filed on Apr. 6, 2009 for U.S. Appl. No. 10/978,556, filed Nov. 1, 2004 (Inventor—B.L. Gibbins).
Final Rejection issued on Nov. 6, 2008 for U.S. Appl. No. 10/978,556, filed Nov. 1, 2004 (Inventor—B.L. Gibbins).
Amendment/Response After Non-Final Rejection filed on Aug. 1, 2008 for U.S. Appl. No. 10/978,556, filed Nov. 1, 2004 (Inventor—B.L. Gibbins).
Non-Final Rejection issued on Apr. 1, 2008 for U.S. Appl. No. 10/978,556, filed Nov. 1, 2004 (Inventor—B.L. Gibbins).
Amendment Submitted/Entered with CPA/RCE filed on Oct. 31, 2007 for U.S. Appl. No. 10/978,556, filed Nov. 1, 2004 (Inventor—B.L. Gibbins).

Advisory Action (PTOL-303) issued on Oct. 3, 2007 for U.S. Appl. No. 10/978,556, filed Nov. 1, 2004 (Inventor—B.L. Gibbins).
Amendment After Final Rejection filed on Sep. 13, 2007 for U.S. Appl. No. 10/978,556, filed Nov. 1, 2004 (Inventor—B.L. Gibbins).,
Final Rejection issued on Jul. 13, 2007 for U.S. Appl. No. 10/978,556, filed Nov. 1, 2004 (Inventor—B.L. Gibbins).
Amendment/Response After Non-Final Rejection filed on Apr. 24, 2007 for U.S. Appl. No. 10/978,556, filed Nov. 1, 2004 (Inventor—B.L. Gibbins).
Non-Final Rejection issued on Jan. 24, 2007 for U.S. Appl. No. 10/978,556, filed Nov. 1, 2004 (Inventor—B.L. Gibbins).
Response to Election / Restriction filed on Nov. 13, 2006 for U.S. Appl. No. 10/978,556, filed Nov. 1, 2004 (Inventor—B.L. Gibbins).
Requirement for Restriction/Election issued on Oct. 11, 2006 for U.S. Appl. No. 10/978,556, filed Nov. 1, 2004 (Inventor—B.L. Gibbins).
Preliminary Amendment filed on Feb. 15, 2005 for U.S. Appl. No. 10/978,556, filed Nov. 1, 2004 (Inventor—B.L. Gibbins).
Reexamination Certificate Issued on Jun. 16, 2009 for Inter Partes Reexam No. 95/000,042 of U.S. Pat. 6,605,751 granted Aug. 12, 2003 (Gibbins et al.).
Notice of Intent to Issue a Reexam Certificate issued on Mar. 25, 2009 for Inter Partes Reexam No. 95/000,042 of U.S. Pat. 6,605,751 granted Aug. 12, 2003 (Gibbins et al.).
Right of Appeal Notice issued on Dec. 9, 2008 for Inter Partes Reexam No. 95/000,042 of U.S. Pat. 6,605,751 granted Aug. 12, 2003 (Gibbins et al.).
Action Closing Prosecution (nonfinal) issued on Aug. 19, 2008 for Inter Partes Reexam No. 95/000,042 of U.S. Pat. 6,605,751 granted Aug. 12, 2003 (Gibbins et al.).
Response after non-final action-owner filed on Oct. 8, 2004 for Inter Partes Reexam No. 95/000,042 of U.S. Pat. 6,605,751 granted Aug. 12, 2003 (Gibbins et al.).
Reexam Ordered and Non-Final Action issued on Aug. 4, 2004 for Inter Partes Reexam No. 95/000,042 of U.S. Pat. 6,605,751 granted Aug. 12, 2003 (Gibbins et al.).
Ex Parte Reexam request filed on May 13, 2004 for Inter Partes Reexam No. 95/000,042 of U.S. Pat. 6,605,751 granted Aug. 12, 2003 (Gibbins et al.).
Communication regarding the expiry of opposition period issued on Apr. 4, 2007 for EP App. No. 990393.1, which claims priority to PCT/US00/35560, filed on Dec. 29, 2000, published Jul. 12, 2001 as WO 01/49258 (Applicant—Acrymed).
Decision to grant a European Pat. issued on Apr. 21, 2006 for EP App. No. 990393.1, which claims priority to PCT/US00/35560, filed on Dec. 29, 2000, published Jul. 12, 2001 as WO 01/49258 (Applicant—Acrymed).
Reply to communication about intention to grant filed on Mar. 28, 2006 for EP App. No. 990393.1, which claims priority to PCT/US00/35560, filed on Dec. 29, 2000, published Jul. 12, 2001 as WO 01/49258 (Applicant—Acrymed).
Communication about intention to grant a European Pat. filed on Nov. 28, 2005 for EP App. No. 990393.1, which claims priority to PCT/US00/35560, filed on Dec. 29, 2000, published Jul. 12, 2001 as WO 01/49258 (Applicant—Acrymed).
Reply to communication from the Examining Division filed on Aug. 30, 2005 for EP App. No. 990393.1, which claims priority to PCT/US00/35560, filed on Dec. 29, 2000, published Jul. 12, 2001 as WO 01/49258 (Applicant—Acrymed).
Communication from the Examining Division issued on Feb. 22, 2005 for EP App. No. 990393.1, which claims priority to PCT/US00/35560, filed on Dec. 29, 2000, published Jul. 12, 2001 as WO 01/49258 (Applicant—Acrymed).
Reply to communication from the Examining Division filed on Apr. 1, 2004 for EP App. No. 990393.1, which claims priority to PCT/US00/35560, filed on Dec. 29, 2000, published Jul. 12, 2001 as WO 01/49258 (Applicant—Acrymed).
Communication from the Examining Division issued on Feb. 13, 2004 for EP App. No. 990393.1, which claims priority to PCT/US00/35560, filed on Dec. 29, 2000, published Jul. 12, 2001 as WO 01/49258 (Applicant—Acrymed).
Reply to communication from the Examining Division filed on Jul. 24, 2003 for EP App. No. 990393.1, which claims priority to PCT/US00/35560, filed on Dec. 29, 2000, published Jul. 12, 2001 as WO 01/49258 (Applicant—Acrymed).
Communication from the Examining Division issued on Jan. 23, 2003 for EP App. No. 990393.1, which claims priority to PCT/US00/35560, filed on Dec. 29, 2000, published Jul. 12, 2001 as WO 01/49258 (Applicant—Acrymed).
Amendments before examination filed on Oct. 18, 2002 for EP App. No. 990393.1, which claims priority to PCT/US00/35560, filed on Dec. 29, 2000, published Jul. 12, 2001 as WO 01/49258 (Applicant—Acrymed).
Amendments before examination filed on Jul. 19, 2002 for EP App. No. 990393.1, which claims priority to PCT/US00/35560, filed on Dec. 29, 2000, published Jul. 12, 2001 as WO 01/49258 (Applicant—Acrymed).
PCT Intl. Search Report issued on Jul. 12, 2001 for PCT/US00/35560, filed on Dec. 29, 2000, published Jul. 12, 2001 as WO 01/49258 (Applicant—Acrymed; Inventors: Gibbins).
PCT Intl. Preliminary Examination Report issued on Apr. 2, 2002 for PCT/US00/35560, filed on Dec. 29, 2000, published Jul. 12, 2001 as WO 01/49258 (Applicant—Acrymed; Inventors: Gibbins).
Non-Final Rejection mailed on Feb. 15, 2011 for U.S. Appl. No. 09/752,939, filed Dec. 29, 2000 (Inventor —Gibbins).
Amendment Submitted/Entered with Cpa/Rce filed on Jan. 18, 2011 for U.S. Appl. No. 09/752,939, filed Dec. 29, 2000 (Inventor—Gibbins).
Notice of Appeal filed on Jun. 17, 2010 for U.S. Appl. No. 09/752,939, filed Dec. 29, 2000 (Inventor—Gibbins).
Final Rejection issued on Feb. 25, 2010 for U.S. Appl. No. 09/752,939, filed Dec. 29, 2000 (Inventor—Gibbins).
Amendment/Response After Non-Final Action filed on Dec. 3, 2009 for U.S. Appl. No. 09/752,939, filed Dec. 29, 2000 (Inventor—Gibbins).
Non-Final Rejection issued on Jun. 4, 2009 for U.S. Appl. No. 09/752,939, filed Dec. 29, 2000 (Inventor—Gibbins).
Amendment Submitted/Entered with CPA/RCE filed on Mar. 16, 2009 for U.S. Appl. No. 09/752,939, filed Dec. 29, 2000 (Inventor—Gibbins).
Final Rejection issued on Sep. 18, 2008 for U.S. Appl. No. 09/752,939, filed Dec. 29, 2000 (Inventor—Gibbins).
Amendment/Response After Non-Final Action filed on Apr. 28, 2008 for U.S. Appl. No. 09/752,939, filed Dec. 29, 2000 (Inventor—Gibbins).
Non-Final Rejection issued on Dec. 28, 2007 for U.S. Appl. No. 09/752,939, filed Dec. 29, 2000 (Inventor—Gibbins).
Amendment Submitted/Entered with Cpa/Rce filed on Oct. 9, 2007 for U.S. Appl. No. 09/752,939, filed Dec. 29, 2000 (Inventor—Gibbins).
Advisory Action (PTOL-303) issued on Sep. 4, 2007 for U.S. Appl. No. 09/752,939, filed Dec. 29, 2000 (Inventor—Gibbins).
Amendment After Final Rejection filed on Aug. 6, 2007 for U.S. Appl. No. 09/752,939, filed Dec. 29, 2000 (Inventor—Gibbins).
Final Rejection issued on Jun. 6, 2007 for U.S. Appl. No. 09/752,939, filed Dec. 29, 2000 (Inventor—Gibbins).
Supplemental Response/Amendment filed on Apr. 3, 2007 for U.S. Appl. No. 09/752,939, filed Dec. 29, 2000 (Inventor—Gibbins).
Amendment/Response After Non-Final Action filed on Feb. 14, 2007 for U.S. Appl. No. 09/752,939, filed Dec. 29, 2000 (Inventor—Gibbins).
Examiner Interview Summary Record (PTOL—413) issued on Jan. 17, 2007 for U.S. Appl. No. 09/752,939, filed Dec. 29, 2000 (Inventor—Gibbins).
Non-Final Rejection issued on Sep. 14, 2006 for U.S. Appl. No. 09/752,939, filed Dec. 29, 2000 (Inventor—Gibbins).
Amendment Submitted/Entered with CPA/RCE filed on Aug. 7, 2006 for U.S. Appl. No. 09/752,939, filed Dec. 29, 2000 (Inventor—Gibbins).
Amendment initialed by Examiner/Advisory Action (PTOL-303) issued on May 18, 2006 for U.S. Appl. No. 09/752,939, filed Dec. 29, 2000 (Inventor—Gibbins).
Amendment After Final Rejection filed on May 8, 2006 for U.S. Appl. No. 09/752,939, filed Dec. 29, 2000 (Inventor—Gibbins).
Final Rejection issued on Mar. 7, 2006 for U.S. Appl. No. 09/752,939, filed Dec. 29, 2000 (Inventor—Gibbins).

Amendment/Response After Non-Final Action filed on Dec. 1, 2005 for U.S. Appl. No. 09/752,939, filed Dec. 29, 2000 (Inventor—Gibbins).
Non-Final Rejection issued on Aug. 2, 2005 for U.S. Appl. No. 09/752,939, filed Dec. 29, 2000 (Inventor—Gibbins).
Amendment Submitted/Entered with CPA/RCE filed on Jun. 15, 2005 for U.S. Appl. No. 09/752,939, filed Dec. 29, 2000 (Inventor—Gibbins).
Advisory Action (PTOL-303) issued on Jun. 8, 2005 for U.S. Appl. No. 09/752,939, filed Dec. 29, 2000 (Inventor—Gibbins).
Amendment After Final Rejection filed on Mar. 30, 2005 for U.S. Appl. No. 09/752,939, filed Dec. 29, 2000 (Inventor—Gibbins).
Final Rejection issued on Dec. 16, 2004 for U.S. Appl. No. 09/752,939, filed Dec. 29, 2000 (Inventor—Gibbins).
Amendment/Response After Non-Final Action filed on Sep. 16, 2004 for U.S. Appl. No. 09/752,939, filed Dec. 29, 2000 (Inventor—Gibbins).
Non-Final Rejection issued on May 17, 2004 for U.S. Appl. No. 09/752,939, filed Dec. 29, 2000 (Inventor—Gibbins).
Decision to Withdraw from Issue issued on Apr. 26, 2004 for U.S. Appl. No. 09/752,939, filed Dec. 29, 2000 (Inventor—Gibbins).
Notice of Allowance issued on Jan. 23, 2003 for U.S. Appl. No. 09/752,939, filed Dec. 29, 2000 (Inventor—Gibbins).
Amendment Submitted/Entered with CPA/RCE filed on Nov. 15, 2002 for U.S. Appl. No. 09/752,939, filed Dec. 29, 2000 (Inventor—Gibbins).
Advisory Action (Ptol-303) issued on Nov. 19, 2002 for U.S. Appl. No. 09/752,939, filed Dec. 29, 2000 (Inventor—Gibbins).
Amendment After Final Rejection filed on Oct. 15, 2002 for U.S. Appl. No. 09/752,939, filed Dec. 29, 2000 (Inventor—Gibbins).
Final Rejection issued on Jul. 15, 2002 for U.S. Appl. No. 09/752,939, filed Dec. 29, 2000 (Inventor—Gibbins).
Amendment/Response After Non-Final Action filed on Apr. 18, 2002 for U.S. Appl. No. 09/752,939, filed Dec. 29, 2000 (Inventor—Gibbins).
Examiner Interview Summary Record (PTOL—413) issued on Apr. 11, 2002 for U.S. Appl. No. 09/752,939, filed Dec. 29, 2000 (Inventor—Gibbins).
Non-Final Rejection issued on Dec. 18, 2001 for for U.S. Appl. No. 09/752,939, filed Dec. 29, 2000 (Inventor—Gibbins).
Issue Notification issued on Dec. 20, 2006 for U.S. Appl. No. 10/441,141, filed May 19, 2003 (Inventor—Gibbins).
Notice of Allowance/Examiner Interview Summary Record (PTOL—413) issued on Jul. 25, 2006 for U.S. Appl. No. 10/441,141, filed May 19, 2003 (Inventor—Gibbins).
Amendment After Final Rejection filed on Jul. 5, 2006 for U.S. Appl. No. 10/441,141, filed May 19, 2003 (Inventor—Gibbins).
Examiner Interview Summary Record (PTOL—413) issued on Jun. 28, 2006 for U.S. Appl. No. 10/441,141, filed May 19, 2003 (Inventor—Gibbins).
Final Rejection issued on May 4, 2006 for U.S. Appl. No. 10/441,141, filed May 19, 2003 (Inventor—Gibbins).
Amendment/Response After Non-Final Action filed on Feb. 14, 2006 for U.S. Appl. No. 10/441,141, filed May 19, 2003 (Inventor—Gibbins).
Non-Final Rejection issued on Nov. 15, 2005 for U.S. Appl. No. 10/441,141, filed May 19, 2003 (Inventor—Gibbins).
Preliminary Amendment filed on Apr. 12, 2003 for U.S. Appl. No. 10/441,141, filed May 19, 2003 (Inventor—Gibbins).
Notification of Grant issued Feb. 5, 2010 for Chinese Pat. App. No. 03820077.5, which claims priority to PCT/US03/023851 filed Jul. 29, 2003, published Feb. 5, 2004 as WO 04/010952 (Applicant—Acrymed, Inc.).
Response to fifth Office Action filed on Jan. 7, 2010 for Chinese Pat. App. No. 03820077.5, which claims priority to PCT/US03/023851 filed Jul. 29, 2003, published Feb. 5, 2004 as WO 04/010952 (Applicant—Acrymed, Inc.) + claims in English.
Fifth Office Action issued on Oct. 23, 2009 for Chinese Pat. App. No. 03820077.5, which claims priority to PCT/US03/023851 filed Jul. 29, 2003, published Feb. 5, 2004 as WO 04/010952 (Applicant—Acrymed, Inc.).
Response to fourth Office Action filed on Sep. 11, 2009 for Chinese Pat. App. No. 03820077.5, which claims priority to PCT/US03/023851 filed Jul. 29, 2003, published Feb. 5, 2004 as WO 04/010952 (Applicant—Acrymed, Inc.)—English translation only.
Decision to Grant pursuant to Article 97(2) EPC issued on Dec. 2, 2010 for EP App. No. 3772113.1, which claims priority to PCT/US03/023851 filed Jul. 29, 2003, published Feb. 5, 2004 as WO 04/010952 (Applicant—Acrymed, Inc.).
Communication under Rule 71(3) EPC issued on Jun. 4, 2010 for EP App. No. 3772113.1, which claims priority to PCT/US03/023851 filed Jul. 29, 2003, published Feb. 5, 2004 as WO 04/010952 (Applicant—Acrymed, Inc.).
Letter during examination procedure after communication from the Examining Division filed on Jan. 19, 2010 for EP App. No. 3772113.1, which claims priority to PCT/US03/023851 filed Jul. 29, 2003, published Feb. 5, 2004 as WO 04/010952 (Applicant—Acrymed, Inc.).
Reply to communication from the Examining Division filed on Jan. 13, 2010 for EP App. No. 3772113.1, which claims priority to PCT/US03/023851 filed Jul. 29, 2003, published Feb. 5, 2004 as WO 04/010952 (Applicant—Acrymed, Inc.).
PCT Intl. Search Report issued on Aug. 27, 2004 for Intl. App. No. PCT/US03/023851 filed Jul. 29, 2003, published Feb. 5, 2004 as WO 04/010952 (Applicant—AcryMed, Inc.).
Issue Notification issued on Jul. 6, 2005 for U.S. Appl. No. 10/207936, filed Jul. 29, 2002 (Inventor—Maley, J. C.).
Amendment/Response-After Non-Final Rejection filed on Apr. 25, 2005 for U.S. Appl. No. 10/207936, filed Jul. 29, 2002 (Inventor—Maley, J. C.).
Office Communication issued on Mar. 30, 2005 for U.S. Appl. No. 10/207936, filed Jul. 29, 2002 (Inventor—Maley, J. C.).
Notice of Allowance and Fees Due (PTOL-85) with Examiner Interview Summary Record (PTOL—413) issued Feb. 16, 2005 for U.S. Appl. No. 10/207936, filed Jul. 29, 2002 (Inventor—Maley, J. C.).
Supplemental Amendment after Final Rejection issed on Jan. 28, 2005 for U.S. Appl. No. 10/207936, filed Jul. 29, 2002 (Inventor—Maley, J. C.).
Amendment After Final Rejection filed on Jan. 12, 2005 for U.S. Appl. No. 10/207936, filed Jul. 29, 2002 (Inventor—Maley, J. C.).
Final Rejection issued on Nov. 23, 2004 for U.S. Appl. No. 10/207936, filed Jul. 29, 2002 (Inventor—Maley, J. C.).
Response After Non-Final Rejection filed on Jul. 29, 2004 for U.S. Appl. No. 10/207936, filed Jul. 29, 2002 (Inventor—Maley, J. C.).
Non-Final Rejection issued on Apr. 29, 2004 for U.S. Appl. No. 10/207936, filed Jul. 29, 2002 (Inventor—Maley, J. C.).
Response After Non-Final Rejection filed on Jan. 22, 2004 for U.S. Appl. No. 10/207936, filed Jul. 29, 2002 (Inventor—Maley, J. C.).
Non-Final Rejection issued on Oct. 22, 2003 for U.S. Appl. No. 10/207,936, filed Jul. 29, 2002 (Inventor—Maley, J. C.).
Second Office Action issued on Aug. 12, 2011 for Chinese Pat. App. No. 200580028750.9, which claims priority to Intl. App. No. PCT/US/05/027260 filed Aug. 1, 2005, published Feb. 9, 2006 as WO 06/015317 (Applicant—Acrymed, Inc.).
Response to First Office Action filed on Jul. 9, 2009 for Chinese Pat. App. No. 200580028750.9, which claims priority to Intl. App. No. PCT/US/05/027260 filed Aug. 1, 2005, published Feb. 9, 2006 as WO 06/015317 (Applicant—Acrymed, Inc.)—Proposed Claims in English.
First Office Action issued on Dec. 26, 2008 for Chinese Pat. App. No. 200580028750.9, which claims priority to Intl. App. No. PCT/US/05/027260 filed Aug. 1, 2005, published Feb. 9, 2006 as WO 06/015317 (Applicant—Acrymed, Inc.).
Amended claims filed on Feb. 26, 2007 for EP App. No. 05778379.7, which claims priority to Intl. App. No. PCT/US05/027260 filed Aug. 1, 2005, published Feb. 9, 2006 as WO 06/015317 (Applicant—Acrymed, Inc.).
Response to Examiners Report filed on Jun. 29, 2011 for Indian Pat. App 735/KOLNP/2007, which claims priority to Intl. Pat. App. No. PCT/US05/027260, filed on Aug. 1, 2005, published on Mar. 9, 2006 as WO 06/015317 (Applicant—Acrymed, Inc.).
Examiners Report issued on Jun. 29, 2010 for Indian Pat. App 735/KOLNP/2007, which claims priority to Intl. Pat. App. No. PCT/US05/027260, filed on Aug. 1, 2005, published on Mar. 9, 2006 as WO 06/015317 (Applicant—Acrymed, Inc.).

Intl. Preliminary Report on Patentability issued on Jan. 30, 2007 for Intl. App. No. PCT/US05/027260 filed Aug. 1, 2005, published Feb. 9, 2006 as WO 06/015317 (Applicant—Acrymed, Inc.).
Intl. Search Report with Written Opinion issued on Apr. 28, 2006 for Intl. App. No. PCT/US05/027260 filed Aug. 1, 2005, published Feb. 9, 2006 as WO 06/015317 (Applicant—Acrymed, Inc.).
Protest Documents from 3rd Party filed on Apr. 3, 2009 for U.S. Appl. No. 11/572,899, filed May 13, 2008 (Inventor—Karandikar et al.).
Preliminary Amendment filed on Jan. 29, 2007 for U.S. Appl. No. 11/572,899, filed May 13, 2008 (Inventor—Karandikar et al.).
Intl. Preliminary Report on Patentability issued on Jan. 30, 2007 for Intl. App. No. PCT/US05/027261 filed Aug. 1, 2005, published Mar. 9, 2006 as WO 06/026026 (Applicant—Acrymed, Inc.).
Intl. Search Report with Written Opinion issued on Apr. 28, 2006 for Intl. App. No. PCT/US05/027261 filed Aug. 1, 2005, published Mar. 9, 2006 as WO 06/026026 (Applicant—Acrymed, Inc.).
Notice of Acceptance issued on Jan. 24, 2011 for AU Pat. App. No. 2005280443, which claims priority to Intl. Pat. App. No. PCT/US05/027261, filed on Aug. 1, 2005, published on Mar. 9, 2006 as WO 06/02026 (Applicant—Acrymed, Inc.).
Response to Examiners Report filed on Dec. 13, 2010 for AU Pat. App. No. 2005280443, which claims priority to Intl. Pat. App. No. PCT/US05/027261, filed on Aug. 1, 2005, published on Mar. 9, 2006 as WO 06/02026 (Applicant—Acrymed, Inc.).
Examiners First Report issued on Feb. 19, 2010 for AU Pat. App. No. 2005280443, which claims priority to Intl. Pat. App. No. PCT/US05/027261, filed on Aug. 1, 2005, published on Mar. 9, 2006 as WO 06/02026 (Applicant—Acrymed, Inc.).
AU Divisional App. No. 2011202034 filed on May 3, 2011 from AU Pat. App. No. 2005280443, which claims priority to Intl. Pat. App. No. PCT/US05/027261, filed on Aug. 1, 2005, published on Mar. 9, 2006 as WO 06/02026 (Applicant—Acrymed, Inc.).
Second Office Action (Text Portion) issued on Jun. 7, 2011 for Chinese Pat. App. No. 200580028877.0, which claims priority to Intl. Pat. App. No. PCT/US05/027261, filed on Aug. 1, 2005, published on Mar. 9, 2006 as WO 06/02026 (Applicant—Acrymed, Inc.).
Response to Office Action filed on Jul. 9, 2009 for Chinese Pat. App. No. 200580028877.0, which claims priority to Intl. Pat. App. No. PCT/US05/027261, filed on Aug. 1, 2005, published on Mar. 9, 2006 as WO 06/02026 (Applicant—Acrymed, Inc.).
First Office Action issued on Dec. 26, 2008 for Chinese Pat. App. No. 200580028877.0, which claims priority to Intl. Pat. App. No. PCT/US05/027261, filed on Aug. 1, 2005, published on Mar. 9, 2006 as WO 06/02026 (Applicant —Acrymed, Inc.).
Response to Examiner's Report filed on Jun. 30, 2011 for Indian Pat. App 397/KOLNP/2007, which claims priority to Intl. Pat. App. No. PCT/US05/027261, filed on Aug. 1, 2005, published on Mar. 9, 2006 as WO 06/02026 (Applicant—Acrymed, Inc.)—proposed amendments only.
Examiners Report issued on Jul. 2, 2010 for Indian Pat. App 397/KOLNP/2007, which claims priority to Intl. Pat. App. No. PCT/US05/027261, filed on Aug. 1, 2005, published on Mar. 9, 2006 as WO 06/02026 (Applicant—Acrymed, Inc.).
Official Action issued on Mar. 1, 2011 for JP App. No. 2007-523881, which claims priority to Intl. Pat. App. No. PCT/US05/027261, filed on Aug. 1, 2005, published on Mar. 9, 2006 as WO 06/02026 (Applicant—Acrymed, Inc.)—translation included.
Notice of Acceptance issued on Apr. 26, 2011 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Response to Examination Report filed on Apr. 21, 2011 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Examination Report issued on Feb. 2, 2011 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Response to Examination Report filed on Jan. 20, 2011 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Further Examination Report issued on Jul. 8, 2010 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Response and Amended Pages filed on Jun. 28, 2010 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Examination Report issued on Apr. 24, 2009 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
NZ Divisional App. No. 592438 filed on Apr. 21, 2011 from New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Examiners first report issued on Oct. 18, 2010 for Australian Pat. App. No. 2007215443, which claims priority to PCT/US07/03390, filed Feb. 8, 2007, published on Aug. 23, 2007 as WO 07/095058 (Applicant—Acrymed, Inc.).
Response to Second Office Action filed on Jun. 7, 2011 for Chinese Pat. App. No. 200780012684.5, which claims priority to PCT/US07/003390 filed on Feb. 8,2007 (Applicant—AcryMed, Inc.)—No Translation.
Second Office Action issued Mar. 23, 2011 for Chinese Pat. App. No. 200780012684.5, which claims priority to PCT/US07/003390 filed on Feb. 8,2007 (Applicant—AcryMed, Inc.).
Response to First Office Action filed on Feb. 28, 2011 for Chinese Pat. App. No. 200780012684.5, which claims priority to PCT/US07/003390 filed on Feb. 8,2007 (Applicant—AcryMed, Inc.)—Proposed amended claims in English.
First Office Action issued Oct. 13, 2010 for Chinese Pat. App. No. 200780012684.5, which claims priority to PCT/US07/003390 filed on Feb. 8,2007 (Applicant—AcryMed, Inc.).
Claim amendments filed on Sep. 4, 2008 for EP App. No. 07750244.1, which claims priority to PCT/US07/03390, filed Feb. 8, 2007, published on Aug. 23, 2007 as WO 07/095058 (Applicant—Acrymed, Inc.).
PCT Preliminary Report on Patentability issued on Aug. 12, 2008 for Intl. Pat. App. No. PCT/US07/03390, filed Feb. 8, 2007, published on Aug. 23, 2007 as WO 07/095058 (Applicant—Acrymed, Inc.).
PCT Intl. Search Report with Written Opinion issued on Dec. 21, 2007 for Intl. Pat. App. No. PCT/US07/03390, filed Feb. 8, 2007, published on Aug. 23, 2007 as WO 07/095058 (Applicant—Acrymed, Inc.).
Amendment Entered with CPA/RCE filed on Apr. 22, 2011 for U.S. Appl. No. 11/704,167 filed Feb. 8, 2007 (Inventors—Karandikar et al.).
Final Rejection issued on Dec. 22, 2010 for U.S. Appl. No. 11/704,167, filed Feb. 8, 2007 (Inventors—Karandikar et al.).
Response after Non-Final Action mailed Oct. 28, 2010 for U.S. Appl. No. 11/704,167, filed Feb. 8, 2007 (Inventors—Karandikar et al.).
Non-Final Rejection issued on May 28, 2010 for U.S. Appl. No. 11/704,167, filed Feb. 8, 2007 (Inventors—Karandikar et al.).
Response to Election / Restriction filed on Apr. 30, 2010 for U.S. Appl. No. 11/704,167, filed Feb. 8, 2007 (Inventors—Karandikar et al.).
Restriction/Election Requirement issued on Mar. 30, 2010 for U.S. Appl. No. 11/704,167, filed Feb. 8, 2007 (Inventors—Karandikar et al.).
Preliminary Amendments filed on Nov. 24, 2008 for EP 07755996.1 which claims priority to PCT/US07/009997, filed on Apr. 25, 2007, published on Nov. 8, 2007 as WO 07/127236 (Applicant—Acrymed, Inc.).
Intl. Search Report w/ Written Opinion issued on Aug. 25, 2008 for Intl. Pat. App. No. PCT/US07/009997, filed on Apr. 25, 2007, published on Nov. 8, 2007 as WO 07/127236 (Applicant—Acrymed, Inc.).
Intl. Preliminary Report on Patentability issued on Oct. 28, 2008 for Intl. Pat. App. No. PCT/US07/009997, filed on Apr. 25, 2007, published on Nov. 8, 2007 as WO 07/127236 (Applicant—Acrymed, Inc.).

Final Rejection issued on Jun. 23, 2011 for U.S. Appl. No. 11/789,701, filed Apr. 25, 2007 (Inventors—McMaken et al.).
Response after Non-Final Rejection filed on Apr. 5, 2011 for U.S. Appl. No. 11/789,701, filed Apr. 25, 2007 (Inventors—McMaken et al.).
Non-Final Rejection issued on Oct. 5, 2010 for U.S. Appl. No. 11/789,701, filed Apr. 25, 2007 (Inventors—McMaken et al.).
Amendment Entered with CPA/RCE filed on Mar. 31, 2010 for U.S. Appl. No. 11/789,701, filed Apr. 25, 2007 (Inventors—McMaken et al.).
Final Rejection issued on Oct. 5, 2009 for U.S. Appl. No. 11/789,701, filed Apr. 25, 2007 (Inventors—McMaken et al.).
Response After Non-Final Rejection filed Jun. 8, 2009 for U.S. Appl. No. 11/789,701, filed Apr. 25, 2007 (Inventors—McMaken et al.).
Non-Final Rejection issued on Jan. 26, 2009 for U.S. Appl. No. 11/789,701, filed Apr. 25, 2007 (Inventors—McMaken et al.).
Response to Election / Restriction filed on Dec. 15, 2008 for U.S. Appl. No. 11/789,701, filed Apr. 25, 2007 (Inventors—McMaken et al.).
Requirement for Restriction/Election issued on Nov. 14, 2008 for U.S. Appl. No. 11/789,701, filed Apr. 25, 2007 (Inventors—McMaken et al.).
Intl. Preliminary Report on Patentability issued on May 24, 2011 for Intl. Pat. App. No. PCT/US09/065764, filed on Nov. 24, 2009, published on May 27, 2010 as WO 10/060094 (Applicant—Kimberly-Clark, Worldwide Inc..).
Intl. Search Report with Written Opinion issued on Apr. 28, 2010 for Intl. Pat. App. No. PCT/US09/065764, filed on Nov. 24, 2009, published on May 27, 2010 as WO 10/060094 (Applicant—Kimberly-Clark, Worldwide Inc.).
Reply to Communication from Examining Division filed on Jun. 16, 2011 for EP App. No. 05797894.2, which claims priority to PCT/US05/033600, filed Sep. 19, 2005, published on Mar. 30, 2006 as WO 06/034249 (Applicant—Acrymed, Inc.).
Communication from Examining Division issued on Feb. 8, 2011 for EP App. No. 05797894.2, which claims priority to PCT/US05/033600, filed Sep. 19, 2005, published on Mar. 30, 2006 as WO 06/034249 (Applicant—Acrymed, Inc.).
Reply to Communication from Examining Division filed on Jun. 23, 2009 for EP App. No. 05797894.2, which claims priority to PCT/US05/033600, filed Sep. 19, 2005, published on Mar. 30, 2006 as WO 06/034249 (Applicant—Acrymed, Inc.).
Communication from Examining Division issued on Dec. 17, 2008 for EP App. No. 05797894.2, which claims priority to PCT/US05/033600, filed Sep. 19, 2005, published on Mar. 30, 2006 as WO 06/034249 (Applicant—Acrymed, Inc.).
Supplemental European Search Report and Opinion issued on Oct. 21, 2008 for EP App. No. 05797894.2, which claims priority to PCT/US05/033600, filed Sep. 19, 2005, published on Mar. 30, 2006 as WO 06/034249 (Applicant—Acrymed, Inc.).
Amendments before examination filed on Apr. 18, 2007 for EP App. No. 05797894.2, which claims priority to PCT/US05/033600, filed Sep. 19, 2005, published on Mar. 30, 2006 as WO 06/034249 (Applicant—Acrymed, Inc.).
Intl. Preliminary Report on Patentability issued on May 1, 2007 for Intl. Pat. App. No. PCT/US05/033600, filed Sep. 19, 2005, published Mar. 30, 2006 as WO 06/034249 (Applicant—Acrymed, Inc.).
Intl. Search Report with Written Opinion issued on Apr. 18, 2007 for Intl. Pat. App. No. PCT/US05/033600, filed on Sep. 19, 2005, published on Mar. 30, 2006 as WO 06/034249 (Applicant—Acrymed, Inc.).

Final Rejection issued on Jun. 13, 2011 for U.S. Appl. No. 11/663,236, filed Mar. 19, 2007 (Karandikar et al.).
Response after Non-Final Action filed on Apr. 12, 2011 for U.S. Appl. No. 11/663,236, filed Mar. 19, 2007 (Karandikar et al.).
Non-Final Rejection issued on Dec. 13, 2010 for U.S. Appl. No. 11/663,236, filed Mar. 19, 2007 (Karandikar et al.).
Response to Restriction/Election Requirement filed on Sep. 23, 2010 for U.S. Appl. No. 11/663,236, filed Mar. 19, 2007 (Karandikar et al.).
Restriction/Election Requirement issued on Jun. 23, 2010 for U.S. Appl. No. 11/663,236, filed Mar. 19, 2007 (Karandikar et al.).
Preliminary Amendment filed on Mar. 19, 2007 for U.S. Appl. No. 11/663,236, filed Mar. 19, 2007 (Karandikar et al.).
Third Office Action issued Jul. 7, 2011 for Chinese Pat. App. No. 200780012684.5, which claims priority to PCT/US07/003390 filed on Feb. 8, 2007 (Applicant—AcryMed, Inc.).
Notice of Allowance issued on May 12, 2011 for U.S. Appl. No. 12/510,651 filed on Jul. 28, 2009 (Inventor—Gibbins).
Amendment/Response After Non-Final Reject/Terminal Disclaimer filed on Apr. 4, 2011 for U.S. Appl. No. 12/510,651, filed on Jul. 28, 2009 (Inventor—Gibbins).
Non-Final Rejection issued on Jan. 5, 2011 for U.S. Appl. No. 12/510,651, filed on Jul. 28, 2009 (Inventor—Gibbins).
Preliminary Amendment filed on Oct. 28, 2009 for U.S. Appl. No. 12/510,651, filed on Jul. 28, 2009 (Inventor —Gibbins).
Response to Restriction Requirement filed on Aug. 9, 2011 for U.S. Appl. No. 11/572,899, filed May 13, 2008 (Inventor—Karandikar et al.).
Restriction requirement issued on Jun. 28, 2011 for U.S. Appl. No. 11/572,899, filed May 13, 2008 (Inventor —Karandikar et al.).
Supplemental European Search Report issued May 23, 2011 for EP App. No. 07750244.1, which claims priority to PCT/US07/03390, filed Feb. 8, 2007, published on Aug. 23, 2007 as WO 07/095058 (Applicant—Acrymed, Inc.).
Non-Final Rejection issued on Jun. 30, 2011 for U.S. Appl. No. 11/704,167, filed Feb. 8, 2007 (Inventors—Karandikar et al.).
Amendment/Response After Non-Final Action filed on Aug. 9, 2011 for U.S. Appl. No. 09/752,939, filed on Dec. 29, 2000 (Inventor—Gibbins).
Non-Final Rejection issued on Aug. 17, 2011 for U.S. Appl. No. 12/510,651, filed on Jul. 28, 2009 (Inventor—Gibbins).
Response after Non-Final Rejection filed on Aug. 26, 2011 for U.S. Appl. No. 12/510,651, filed on Jul. 28, 2009 (Inventor—Gibbins).
Amendment Entered with CPA/RCE filed on Feb. 19, 2010 for U.S. Appl. No. 11/194,951, filed Aug. 1, 2005 (Inventor—Karandikar et al.).
Notice of Appeal filed on Oct. 21, 2009 for U.S. Appl. No. 11/194,951, filed Aug. 1, 2005 (Inventor—Karandikar et al.).
Final Rejection issued on May 21, 2009 for U.S. Appl. No. 11/194,951, filed Aug. 1, 2005 (Inventor—Karandikar et al.).
Response After Non-Final Rejection filed on Feb. 5, 2009 for U.S. Appl. No. 11/194,951, filed Aug. 1, 2005 (Inventor—Karandikar et al.).
Non-Final Rejection issued on Aug. 5, 2008 for U.S. Appl. No. 11/194,951, filed Aug. 1, 2005 (Inventor—Karandikar et al.).
Response to Election / Restriction filed on Feb. 5, 2008 for U.S. Appl. No. 11/194,951, filed Aug. 1, 2005 (Inventor—Karandikar et al.).
Requirement for Restriction/Election issued on Dec. 5, 2007 for U.S. Appl. No. 11/194,951, filed Aug. 1, 2005 (Inventor—Karandikar et al.).,

* cited by examiner

METHODS AND COMPOSITIONS FOR TREATMENT OF DERMAL CONDITIONS

PRIOR RELATED APPLICATIONS

The present application is a continuation-in-part of U.S. patent application Ser. No. 10/207,936, filed Jul. 29, 2002 now U.S. Pat. No. 6,921,529, which is incorporated herein in its entirety.

FIELD OF THE INVENTION

This invention discloses methods and compositions for the treatment of dermal conditions. Particularly, this invention relates to treatment of pathological dermal conditions using a variety of topical delivery vehicles to provide active agents to the site or sites of pathology.

BACKGROUND OF THE INVENTION

The dermal structures of humans and other animals are often the site of infections or attachments by other living organisms. Dermal structures include, but are not limited to, skin, hair, hair follicles, cornea, sclera, organ linings, pleural coverings, dura, toenails, fingernails, hooves, horns, mucous membranes, and other cellular structures made from epithelial cells or keratinized structures. Organisms that live in or on the dermis or dermal structures of humans and animals include microorganisms such as yeasts, fungi, bacteria, viruses, mycoplasma, and insects such as dust mites, ticks, lice and other arthropods.

The presence of these organisms in and on dermal structures often cause a range of changes, from merely unsightly to pathological conditions, to the dermis and dermal structures, and can interfere with the functions of the dermis and dermal structures of the host organism. Additionally, the presence of these organisms can result in immunological responses by the host and cause secondary problems at the site or a general response throughout the entire host organism. Thus, there is a need to prevent infection or attachment by such organisms, control the amount of infection or attachment by such organisms, treat the affected sites, and prevent the re-infection and re-attachment by such organisms from the environment.

One of the most common and difficult to treat dermal conditions is infection of nail structures. The finger and toenails of humans are specialized tissue structures that are closely related to claw and hoof tissues in animals. The nails constitute an important protective structure at the distal ends of the fingers and toes that shield the highly sensitive extremities from triggering pain or sensation on contact with the external environment. Nails also function as an important tool that is used to increase the range of dexterous accomplishments. Humans have developed great pride in the function and appearance of nails. In many cultures, painting and decoration of the nails of both the hands and feet are common place.

Nails, like most anatomical structures of the body, are susceptible to disease processes. One of the pathological conditions that is common for humans is caused by microbial invasion of the nail or surrounding tissues. Although the condition is not life threatening, infection of these tissues can compromise the appearance and the function of the affected nail. One such condition results from the invasion of the tissues by one or more of several fungi. Fungal involvement in nail infection has been termed onychomycosis.

Onychomycosis, or fungal infection of the nail, is the most common cause of nail dystrophy. The incidence of the condition has been difficult to determine largely because it is not life threatening and rarely is reported. It has been estimated that the incidence ranges from 3% to 23% of the total population in western cultures. There is no clear understanding of the circumstances that predispose to this condition. It has been suggested that there is a relationship between trauma to the nail region and the occurrence of infection. However no studies have confirmed this hypothesis.

It is known that certain lifestyle and climatic situations seem to contribute to onychomycosis. One example is the greater than 80% occurrence rate of onychomycosis in the general population in outlying northeastern areas of Russia where long cold winters are encountered. This is likely due to the necessity of using heavy protective footwear for prolonged periods to protect the feet from the cold. This exposes the foot, and more particularly the nails, to prolonged moist warm conditions that may encourage the growth of the fungi.

In western cultures it is well known that there is an age related distribution in the incidence of onychomycosis. The condition is much more prevalent in elderly individuals. Indeed it has been estimated that 80 to 90% of the elderly in the U.S. and Canada have at least one or more of their nails involved. One reason for the increase with age is that onychomycosis poorly responds to treatment, hence is seldom treated so there is an accumulation of cases. Other factors that may contribute to the increase with age are a general waning of innate and specific immunity to fungal pathogens as well as an increased accumulation of comorbidities that may contribute to invasion by the fungal pathogens associated with onychomycosis.

Onychomycosis is a dystrophic condition of the nails of the feet and hands. Fungal infection of the nails results in characteristic changes in the appearance to the structure. The appearance is often used to describe the degree of severity of the infection. Clinicians often use appearance alone in differential diagnosis of the condition. Knowledge of the state of the disease is often useful in determining the course of treatment and the likelihood of success in the management of the disorder. The common forms of the disease are listed in Table 1.

TABLE 1

| State of disease | Tissue involve | Severity |
|---|---|---|
| Distal Lateral Subungual Onychomycosis (DLSO) | Fungal invasion at the extreme distal end of the nail bed. | Superficial |
| Proximal Subungual Onychomycosis (PSO) | Fungal invasion at the proximal end of the nail bed. | Superficial to severe. Most often in immunocompromised people. |
| White Superficial Onychomycosis (WSO) | Nail plate only resulting in discrete to extensive white patches or streaks in the nail. | Superficial to severe. |
| Total Dystrophic Onychomycosis (TDO) | Entire nail bed involved. | Severe. |
| Endonyx | Partial or complete involvement of nail plate. | Superficial to severe. |

These different presentations are important in predicting the outcome of a treatment strategy. The anatomy of the nail and its supporting structures profoundly influence the effectiveness of treating the tissues to rid them of the fungal pathogens. The reason for this is that nail structure and anatomy are complex and, to some degree, are isolated from systemic circulation. Furthermore the nail plate is relatively impermeable to penetration by topical agents.

The anatomy of the human nail is important for the understanding of the process that results in onychomycosis. The nail unit is a form of specialized epidermal tissue. The nail apparatus, which comprises all the elements colloquially referred to as "the nail", is composed of distinct structural elements. The most prominent structure of the nail apparatus is referred to as the nail plate which is a thin hard flexible structure that emerges from skin folds at the extremities of the digits. The nail plate is produced by the nail matrix situated in the proximal fold. The matrix causes nail plate elongation through proliferation of its epidermal-like cells. The lateral folds hold the nail plate in an orientation so that elongation proceeds towards the distal end of the extremity. The nail plate grows at the rate of 1 mm (toe nail) to 3 mm (fingernail) per month. The nail plate is translucent in appearance, almost always convex in shape and approximately 0.2-0.6 mm thick. It is composed of approximately 25 layers of dead, keratinized cells that originate from the matrix. These dead cells are held tightly together by intercellular linkages resulting in a coalescent dense hard plate with a smooth dorsal surface. The ventral side of the nail plate is relatively irregular which facilitates attachment of collagen fibers which serve to anchor the nail plate to the nail bed. Nail plate elongation continues toward the distal end of the digit where it parts from the nail bed at a point termed the hyponychium.

The nail plate, chemically, is largely protein along with approximately 10-30% aqueous moisture. Moisture content in the nail plate is directly proportional to the moisture content of the environment. Immersion in water will increase moisture content as will occlusion of the surface so as to prevent evaporation. The nail plate also contains between 0.1 to 1% lipid. There is no central circulation or lymphatic drainage associated with the nail apparatus. However the tissues proximal and lateral, and those beneath the nail bed are highly vascularized. Notwithstanding, the matrix is the only viable component of the nail and is the only structure supported by systemic circulation. The remainder of the nail apparatus is non-viable and is separated from systemic support by a layer of collagen fibrils and nail plate substrate.

Under normal circumstances the nail plate and hyponychium present a formidable barrier to microbial penetration. Indeed, most cases of onychomycosis originate in the distal area of the nail which implies a disturbance to the tight junction at the hyponychium. This probably provides fungi access to the region beneath the nail plate that is rich in organic substrate sufficient to support the growth of the fungi. Less frequent, is the direct fungal penetration into the nail plate. *Trychopyton mentagrophytes* can invade in this way because it produces enzymes that are capable of degrading the protein matrix of the nail plate, thereby enabling the fungus to penetrate directly into the substrate. In either case the fungi enter a privileged region that is largely devoid of natural resistance mediated by the immune system since there is no systemic circulation to the tissues. Moreover, the absence of circulation also restricts the ability of delivering systemic anti-microbial agents effectively to the specific sites where the fungi inhabit.

Onychomycosis is an active disease process that involves the growth and replication of saprophytic fungi in the nail apparatus. Most often the fungi are in the non-viable region between the nail plate and the nail bed. Accurate diagnosis of the condition requires the microscopic examination and culturing of specimen material taken from the affected region. Typically scrapings from the site of infection are first digested in a strong solution of KOH, mounted on microscope slides with a suitable stain specific for fungal mycelium, and then visualized for typical structures common to dermatophytes. In addition, differential diagnosis is greatly enhanced by propagation and identification of fungi using in vitro culturing methods. However, microscopic examination and in vitro culture are time consuming and expensive. Therefore many clinicians will make an imperical diagnosis based on the appearance of the affected nails, lifestyle factors, and age of the individual. This approach may lead to a misdiagnosis of cases resulting in inappropriate and dangerous treatment modalities. There is need for a treatment that is safe and economical that can be implemented with little or no risk should the original diagnosis be incorrect.

The current systemic and the topical methods for the management of onychomycosis are expensive, have low success rates and in many cases expose the user to considerable risk of central organ damage. This is predominately due to the need to deliver sufficient active agent to the individual to achieve an inhibitory concentration in the non-viable regions where the fungi resides. In most cases delivery and accumulation of the active agent is dependent upon diffusion through non-viable and non-vascularized substrate (nail plate, or anchor protein zone of the nail bed). This often has meant persistent administration of the agent with its concomitant risk of systemic toxicity.

The alternative to a direct attack on the fungi is the removal of its privileged habitat. This can be accomplished by removal of the nail plate which provides both nutrient substrate and protection to the fungal parasite. Surgical ablation is still recommended by some as quicker, and better accepted than chemical ablation which is essentially painless. Others condemn it and say chemical ablation is the only way it should be done. Chemical ablation is done by covering the skin around the nail for protection and then applying 40% urea to the nail. An occlusive dressing is then put on and left for a week at which time the patient returns to the doctor for removal. The expense includes a minimum of two doctor visits plus the "procedure" cost. It is effective at removing the nail but it is known to have a fairly high failure rate unless combined with drug treatment. Furthermore it requires between 6 months to a year for the complete outgrowth of new nail plate and a return to a normal appearance of the nail apparatus. It is also somewhat controversial as to its effectiveness as there are no studies showing actual incidence of cure.

The use of oral drugs has lead to the achievement of excellent penetration and accumulation of active agents within the nail after prolonged (months) duration of drug administration. Topical administration has also resulted in good penetration and accumulation of the active. Drug levels have been recorded by direct assay for the active agents, yet in both topical and oral administration there has been a dismal record of cure rate. Complicating evaluation of true cure rate is that "cure" has been ill-defined. In some studies it is taken to mean the achievement of a normal looking nail apparatus whereas in other cases it is taken to mean the elimination of microscopic or culture detectable fungi in specimens collected from the treatment site. Regardless of the method of assessment there is clear recognition that the high cost of treatment, the poor level of outcome, and the concomitant risk of side effects from the therapy have identified that there is a need for a safe, effective, and economic treatment modality for onychomycosis.

There is also a need for treatments for other dermal conditions that are easily used and applied by patients because the treatment times are often long and extended. An ideal treatment modality for onychomycosis and other dermal pathologies would be effective and sufficiently straightforward so that it encourages a high degree of patient compliance. A simple and relatively short duration of administration of an agent targeted for the organism responsible for the pathology should be highly effective at controlling or eliminating the disease-state. Effective topical treatment of the conditions requires successful penetration of the active agent through the nail plate or dermal layers to the zone most commonly harboring the organism. An effective treatment would include the penetration and accumulation/maintenance of an effective concentration of active agent in the growth site and habitat of the unwanted organism.

Compositions are needed that are effective for treatment of unwanted organisms causing pathological conditions in the skin and dermal structures. Such compositions can be used in methods for preventing infection or attachment, treating existing conditions, and preventing re-infection or re-attachment of organisms in the environment. Such compositions should be well tolerated by the patients.

DESCRIPTION OF THE INVENTION

The present invention is directed to methods and compositions for the treatment of dermal conditions. The compositions comprise topical delivery vehicles such as solid matrices, hydrogels, creams, gels and other solutions comprising one or more active agents in effective amounts to treat skin disorders and conditions. Methods of the present invention comprise application of the compositions to affected areas of skin or dermal structures so that the one or more active agents are delivered in an amount effective to treat altered dermal areas or prevent infection or attachment of organisms to a skin area or dermal structure.

As used herein, skin, dermal or dermal structures refers to the elements of the integumentary system of humans and animals, including organ and cavity linings, such as pleura, dura, and pericardium, and mucous membranes and such terms are herein used interchangeably. The integumentary system as it is commonly understood by those skilled in the art refers to the skin, including the epidermis and dermis, which comprise layers including stratum basale, stratum spinosum, stratum granulosum, stratum lucidum, stratum corneum, papillary layer and reticular layer. Cells which are found in these dermal structures include, but are not limited to, keratinocytes, fibroblasts, melanocytes, dendritic cells, Landerhans' cells, epithelial cells, and Merkel cells. Dermal structures include appendages such as hair, sebaceous glands, sweat glands, follicles, nerve structures, horns, hooves and nails.

One embodiment of the invention comprises compositions and methods for treating fungal mediated nail infections referred to as onychomycosis. A composition comprises a matrix material that comprises one or more therapeutic agents, latent moisture, one or more humectants, and may further comprise means to secure the matrix in direct contact with a nail plate.

Though not wishing to be bound by any particular theory, it is thought that a delivery vehicle such as a polymerized matrix structure would provide a reservoir comprising one or more active agents, water and a humectant composition that will be delivered to the nail plate when secured to the nail. The moisture and humectant that are transferred on application to the nail will hydrate the nail plate and form a diffusion gradient for the effective delivery of the active agent to the non-viable areas of the nail apparatus.

Dermal structures are infected by or provide a growth site for a variety of organisms and the methods of the present invention comprise treatment of dermal structures affected by such organisms. Such organisms include organisms that live in or on the epidermis, dermis or dermal structures of humans and animals including, but not limited to microorganisms such as yeasts, fungi, bacteria, viruses, mycoplasma, and insects such as dust mites, ticks, lice and other arthropods.

Organisms termed fungi include a diverse group of free living organisms that include molds, smuts, mushrooms, mildews and yeast. Collectively these organisms are referred to as heterophils, meaning that they utilize non-living complex organic substances as their source of nutrients. These organisms play an important role in the recycling of dead and decaying organic matter in nature. A few fungi have adapted to a saprophytic relationship with higher organisms such as man. Even fewer of these are capable of invading to establish in the unique ecological zone of the nails of mammals. Although a diverse number of fungi have been described in association with nail dystrophy and other dermal pathologies, the vast majority of cases in the U.S. and Canada are caused by a group of fungi known as dermatophytes. Dermatophytes have one property in common; that being that they all are capable of invading and establishing residence in the tissues associated with the skin. Often fungal infection of the skin is referred to as ringworm and the phrase "ringworm of the nails" has been used to describe onychomycosisis. The principle nutrient source for dermatophytes in skin and nails is keratinized proteins. Keratin is non-viable matrix protein complexes derived from epidermal tissues. Typically dermatophytes do not invade beyond the non-viable keratinized layers. Although dermatophytes constitute 90- 96% of the cases of onychomycosis, other fungi such as yeasts and molds have also been found in association with the disease.

The predominate isolates from infected nails has been *Trychophyton rubrum* followed thereafter by *Trychophyton mentagrophytes*, Epidermophyton sp. and Microsporum sp. Non-dermatophyte molds that are occasionally isolated include *Aspergillus niger* and *Scopulariopsis brevicaulis*. Collectively these less frequently encountered fungi account for less than 4-5% of cases. Even less frequently encountered are yeast. The most common yeast isolate is *Candida albicans* which accounts for 3-4% of the total cases. Interestingly, the *C. albicans* onychomycosis is more frequent in women than in men, most often affecting their fingernails.

The cell wall of fungi is primarily chitin, a natural long chain polysaccharide composed largely of poly-(N-acetyl glucosamine). Chitin is extensively distributed in nature, making up the predominate component of the exoskeletons of crabs, spiders and many other creatures. The cell membranes of fungi are similar to the cell membrane structure of human cells except that fungal cell membranes contain ergosterol and zymosterol unlike the cholesterol found in mammalian cell membranes. This is an important difference that has allowed the targeting of specific anti-fungal treatments. All current anti-fungal agents are based on disrupting the biosynthesis of these sterols.

The biosynthesis of squalene to ergosterol is depicted as: Squalene→Squalene epoxide→Lanosterol→14 Dimethyl Lanosterol→Zymosterol→Fecosterol→Episterol→Ergosterol.

There are several anti-fungal compounds that have been extensively evaluated for their activities against fungi and in particular, the dermatophytes which are associated with onychomycosis. TERBENAFINE is an allylamine which blocks the conversion of squalene to squalene epoxide. This results in the accumulation of squalene in the cell. Squalene is an important intermediary compound in ergosterol synthesis but in higher concentrations becomes toxic for the fungi as it accumulates inside the cytoplasm. Lamisil® is the trade name for terbinafine and is considered the most effective oral medication for onychomycosis. It has an advantage over others in that it is also the least likely to cause serious side effects following prolonged usage. Its basis for effectiveness is that it is fungicidal whereas the other agents are fungistatic. TERBINAFINE is less effective for yeast and to some extent molds. It persists for several months after treatment and can be detected in the nail bed at one week. Clinical cure rate is 37% of cases of the total dystrophic onychomycosis (TDO) form of infection. Serious side effects include liver damage and severe generalized skin reactions such as the Stevens-Johnson's syndrome requiring hospitalization. While serious side effects are not common, there were 11 deaths and 2 liver transplants reported to the US government by 2001 out of 16 cases of liver failure. At a 37% cure rate for TDO of the great toe and typically six months treatment required, the overall cost per cure is around $6,500.

Azol antifungals such as ketoconazole, itraconazole, and fluconazole all block the conversion of the intermediate, lanosterol to 14-dimethyl lanosterol. This process starves the cell of intermediates for the synthesis of ergosterol. SPORANOX is the trade name for itraconazol which has been used for the treatment of onychomycosis. It has been generally shown to be less effective than TERBINAFINE in most studies, both in rate of cure and in the relapse rate. It is commonly given as a "pulse", i.e., one week on and three weeks off the oral medication. It is more effective than TERBINAFINE against molds and probably against yeast forms but less effective against dermatophytes. Clinical cure rate with TDO is about 27%. There is a probable association of pulmonary edema with SPORANOX with 58 cases as of 2001 including 13 deaths reported. There were 24 cases of liver failure with 11 deaths from SPORANOX reported to the FDA through 2001. If given daily, the cost is the same as LAMISIL at about $10/tablet or capsule. The cost is less if "pulse treatment" is used. SPORANOX requires regular liver enzyme function monitoring to provide early detection of hepatic injury due to the therapy as is the case for LAMISIL. DIFLUCAN (fluconazole) commonly used for vaginitis is particularly effective against yeast forms (Candida). It persists in the nail plate for several months after treatment. The cure rate for total dystrophic onychomycosis (TDO) is about 38%. It, like LAMISIL and SPORANOX, is also approximately $10/pill and is a once per day dose but can be used with "pulse treatment" like itraconazole. Ketoconazole and Griseofulvin are no longer recommended for onychomycosis.

Amorolfine blocks conversion of intermediates at two sites in the synthetic pathway. It blocks both at the conversion of 14-dimethyl lanosterol to zymosterol and at the conversion of fecosterol to episterol. Again this has the effect of limiting cell membrane synthesis and leads to the selective killing of the fungi dependent upon this pathway. LOCERYL is an amorolfine that is used topically as a 5% solution and is approved for use in Europe for treatment of onychomycosis. It is indicated for mild onychomycosis with no matrix involvement and is effective in about 40% of the cases.

PENLAC (ciclopirox olamine) is the only FDA approved topical treatment for onychomycosis. It is a topical anti-fungal that is painted on the nail, typically once or twice a day for a year or more. It has been recommended for use in combination therapy involving topical plus oral application. In vitro, it is fungicidal against dermatophytes, yeast and molds that typically cause onychomycosis. In a study of mild to moderate distal lateral subungual onychomycosis (DLSO) form of the disease (an average of 40% of nail involved and no matrix infection), it had a 7% cure rate. At $420 per treatment for the drug cost, coupled with a 7% cure rate, extrapolates a cost per cure of almost $8,500 presuming three office visits per patient.

Many individuals with nail dystrophic conditions have turned to alternative concoctions in search of a cure. Tea tree oil (Melaleuca alternafolia) has been claimed to be effective as a "natural" treatment. The only clinical study available is one using it as the "control". There were no cures in the control group of that study. Other alternative treatments advertised include Varisi (50% citrus seed extract, 25% ascorbic acid and 25% glycerin) and Nonyx Gel (acetic acid 9.75%) topically applied daily. Again there is little controlled clinical study information available for either of these and they logically would be unlikely to be effective.

Anti-fungal agents are specifically targeted to interfere with metabolic function of fungi and this can be repeatedly demonstrated under laboratory conditions. However known agents delivered either topically or systemically or, in some cases, as a combination have a low success rate. In theory, these drugs should have a cure rate that approaches 100% success. Some of the factors contributing to the low success rate are:

1. Nail matrix involvement in the condition where it is difficult to penetrate and deliver topical agents at effective concentrations.
2. Penetration of the anti-fungal into the areas were it can be active in controlling fungal growth is problematic. The lateral borders of the nail are exceptionally difficult regions to cause the accumulation of effective levels of actives regardless of whether oral agents or topical agents are used.

Presence of a dermatophytoma, a thick mass of keratin debris between the nail plate and bed, which contributes to poor penetration of either oral or topical drugs into the nail apparatus.

3. Progression of the dystrophic condition to a state known as oncholysis whereby the nail plate detaches from the nail bed resulting in poor penetration and accumulation of oral or topical drugs.
4. There are at least 21 variants of *T. rubrum* which is the predominant causative parasite of onychomycosis. It is possible that some may be more resistant to some treatments.
5. Fungal arthrospores are a dormant state of the fungi and are relatively resistant to anti-fungal agents.
6. An individual's compliance to a treatment regime is singularly difficult to maintain and is likely a major contributor to poor success rates with all current modalities. All current treatments require long periods with (usually) daily intervention to accomplish resolution of the infection. One survey showed a 48% incidence of a failure to adhere to the treatment schedule and 25% of individuals stopped completely before the end of scheduled therapy, often because they thought they were cured and didn't need it any more even though they did.
7. Ineffective elimination of fungi from vectors such as footwear, flooring and bathing surface, and keratinized skin layers results in continuous recurrent introduction of the fungi.

The nail apparatus presents unique challenges. Penetration of active substances, regardless of whether it is from systemic or topical application is dependent upon the movement of the agent through non-viable tissues where the fungi reside. It is likely that the most effective method of distribution through this type of environment would be through diffusion. Moisture or lipid provide the only fluid phase components in the nail apparatus that can support diffusive distribution of the agent. Unfortunately neither of these fluid phase components is in abundant concentrations within the nail plate and nail bed substrates to be exploited for effective delivery of actives. Furthermore the typical infected nail plate is usually considerably thickened in response to fungal activity and therefore presents a greater barrier to diffusion through the small amount of normal latent moisture in the nail.

Fortunately the nail plate is hydrophilic and will readily absorb moisture into the substrate. Therefore either exposure to moisture or, conversely, the use of agent(s) that attract moisture from the surrounding environment can substantially increase the moisture content of the nail plate. This would then provide a diffusion gradient for the transport of an antifungal agent into the sub-plate matrix to act on the fungi. It is known that penetration of compounds through the nail plate can be considerably enhanced by increasing the moisture content in the plate matrix. Therefore a device that incorporates both the active agent(s) and a moisture management system in a reservoir fashion would represent an improvement on previous devices that have been described for aiding in the treatment of onychomycosis.

The majority of onychomycosis involves invasion of the fungi into the bed of the nail. The exceptions are associated with some yeast and molds, and most of the cases secondary to *Trychopyton mentagrophytes* involve the actual nail plate. The invasion of the hard, devitalized keratin structure of the nail plate is assisted by enzymatic degradation of the substrate. This capability is most notable in *T. mentagrophytes* which has enzymes that allow it to digest the nail plate which opens a tract for the saprophyte to gain access into the deeper regions of the structure. Other organisms may also follow its course to establish a co-incident infection below the surface. In advanced stages of onychomycosis both the plate and bed are usually involved. While permanent injury to the bed or matrix will result in permanent loss of the nail plate, most fungal infections do not cause permanent damage. With resolution of the infection, a normal nail can usually be restored by outgrowth of new nail plate structure.

There is a clear differential in the distribution of the disorder between toe and finger nails. Toenails are at least four times more commonly involved than fingernails. One reason may be that the warm, moist environment provided by shoes and stockings is optimal for the growth of dermatophytes. Other factors that may contribute to the increased incidence in toenails is that they are slower growing, are less frequently subjected to cleansing practices, and are continually assaulted with fungi that inhabit footwear. This is supported by the finding that onychomycosis is co-incident with dermatophyte infections elsewhere on the individual. Approximately a third of people with tinea pedis, or athletes' foot will develop onychomycosis.

Adjuvants to attempt enhanced delivery of active agents through the nail plate are not novel. U.S. Pat. Nos. 5,840,283 and 5,972,317 describe the use of a proteolytic enzyme in conjunction with a medication for the treatment of nail fungus. Moisture may be another useful agent for facilitating the movement of active agents through the nail plate. Compositions of the present invention may further comprise a humectant which will attract aqueous moisture from the atmosphere as well as that which is transpired normally into the nail plate. An embodiment of a humectant of the present invention would be of sufficient low molecular size to penetrate and localize in the nail plate so that moisture attracted to the humectant will also localize in the nail.

Numerous organic compounds and salts act as humectants or water retention agents. Humectants may include but not necessarily be limited to any of several organic alcohols such as glycerol, butanol, propanol, isopropyl alcohol, ethanol, methanol, propylene glycol, polyethylene glycol, ethylene alcohol, and butyl alcohol. In addition, several salts, including but not limited to sodium chloride, lithium chloride, copper chloride, magnesium chloride, magnesium sulfate, mangenese sulphate, aluminum sulfate, zinc sulfate, and zinc chloride may function as water retention agents to assist in the hydration of the matrix. In the present invention, the preferred humectant is an organic alcohol since these are well tolerated by tissues yet are of sufficiently small molecular size as to readily migrate with the moisture into the nail plate matrix. The most preferred organic alcohol is glycerol, in concentrations ranging from 4 to 40 percent total weight of the composition. Though not wishing to be bound by any particular theory, it is believed that the humectant is helpful to the composition as it serves to both attract and cause the deposition of moisture in the composition as well as to preserve the aqueous moisture component to prevent loss by evaporation. It is intended that embodiments of the invention, when placed and secured to the nail plate, will deliver aqueous moisture into the plate to form the diffusion gradient of the active agent in the material. Equilibrium of distribution should then result in uniform concentration throughout the composition of the invention and the nail plate. It is also known that increased hydration of the nail plate increases the permeability of materials of varying molecular weights through that substrate. Therefore an added benefit of the incorporation of a humectant such as an organic alcohol, an example being glycerol, would assist in the penetration of agents of a variety of molecular sizes through the nail plate.

The present invention comprises compositions comprising a matrix that will provide molecular space for the incorporation of one or more active agents along with the moisture and one or more humectants during production of the product. Moreover, the composition of the material should be suitable for delivering the material from the matrix to the nail plate upon application during treatment. A suitable component would be any component that is composed of a flexible material that will conform to the contours of the nail. The material also should be capable of containing an effective amount of aqueous moisture to form a diffusion gradient between the matrix and the site of application, when applied, as well as comprise the other components of the delivery system until they function during the application.

Numerous substrates may be suitable for matrices. These include natural and synthetic hydrophilic polymers that may include, but are not limited to, rubber, collagen, animal hide, hyaluronic acid, dextran, alginates, cellulose, carboxymethycellulose, hydroxymethycellulose, elastomers, polyethylenes, polypropylenes, polybutyrate, polyacrylate, polyacrylamide, polybuterate, polyurethane foam, silicone elastomer, nylon, vinyl or cross linked dextran. If cross-linked dextran is used, it is preferred that the molecular weight of the dextran polymer is between 50,000 and 500,000. The polymeric structure of the scaffolding of the invention may either be of a cross-linked or non-cross linked polymer. A preferred embodiment is composed of a cross-linked polymer of the polyacrylate family of polymers. A most preferred embodiment is cross linked polyacrylamide. as it possesses carrying capacity for moisture, active agents and humectant and is non-degradable so that it will persist through the application and treatment phase. An example of such a polyacrylamide matrix is taught by U.S. Pat. No. 5,196,190 to Nangia, et al., which is herein incorporated in its entirety.

Another component of the embodiments of the present invention is a novel anti-fungal agent. It is intended that an embodiment of the present invention is used for the delivery of one or more of the known or contemplated anti-fungal agents, provided that the one or more agents are capable of distribution via diffusion in an aqueous gradient. In addition to known therapeutic anti-fungal compounds, it is known that many other substances are capable of inhibiting or killing dermatophytes. In certain in vitro culture methods, it has been found that increasing the acidity is useful in controlling the growth of dermatophyte fungi. Low pH (i.e., high hydrogen ion concentration) prevents the growth of dermatophytes which are the principle group of fungi responsible for onychomycosis. The present invention comprises compositions comprising one or more acidic agents that are capable of increasing the hydrogen ion concentration of the medium. A preferred source of acidity in the composition is a weak organic acid.

In the present invention it is contemplated that weak organic acids can achieve relatively low pH values in aqueous gradients yet are well tolerated when in contact with tissues. There are numerous suitable organic acids, including but not limited to, citric acid, sorbic acid, ascorbic acid, salicilic acid, tannic acid, succinic acid, lactic acid, pyruvic acid, alpha ketoglutaric acid, glutamic acid, acetic acid and butaric acid. Salicylic acid has both keratinolytic properties as well as being a proton donor. Other anti-mycotic active agents include, iodine, DMSO, azole derivatives, undecylenic acid, tea tree oil, and urea.

A preferred embodiment of the composition comprises at least one active agent, wherein at least one active agent is citric acid. Citric acid is a preferred organic acid because it has 3 carboxyl residues which have distinct pK values for dissociation of protons into the aqueous environment. Therefore the buffered pH can be maintained at a relatively low level through out the application period. Furthermore, citric acid is generally regarded as safe.

A preferred embodiment comprises sufficient citric acid to achieve and maintain a concentration between 0.1-10% w/w citric acid in the non-viable portions of the nail apparatus after equilibration of the diffusion gradient established by the moisture delivered by the matrices of the present invention. Ideally the matrix would contain between approximately 1 and 20% citric acid to accomplish this. More preferably the matrices would possess a concentration between 5 and 15 percent with the most preferred embodiment having between 7 and 13 percent citric acid incorporated in the matrix.

An additional component of embodiments of compositions of the present invention is a moisture management system that is integral to the matrices. The moisture management system may include substances that attract and hold moisture in the matrix. Mucopolysaccharides interact with moisture, which results in hydration of their polymeric structure. Water is often referred to as being "bound" to the polysaccharide. This loose binding of water serves to enable mucopolysaccharides to provide a reservoir effect so that water can be incorporated until another drier substance can take it away. Many polysaccharides may play this role but useful ones for the purpose of the invention would be those that do not gel when exposed to excess water. Numerous polysaccharides may serve the functional purpose of the mucopolysaccharide in the present invention including but not limited to acacia, distarch adipate, alginic acid, agar, arabinogalactan, carrageenan, locust bean gum, methylcellulose, eucheuma seaweed, xanthan gum. One such mucopolysaccharide is derived from the Guar tree and is referred to as guar gum. A range of guar gum between approximately 0.01 kg to 100 kg, preferably between approximately 0.1 kg to 10 kg, and most preferably between approximately 0.5 kg to 2 kg is generally sufficient. Other non-gellable polysaccharides and galactomannan macromolecules include but are not limited to lucerne, fenugreek, honey locust bean gum, white clover bean gum and carob locust bean gum. A preferred embodiment of compositions of the invention would contain guar gum for the purpose of holding water in the substrate.

An embodiment of the compositions of the present invention includes compositions that are capable of being affixed to the site of infection or growth of the unwanted organism, and the compositions are affixed by attachment elements. The utility of the device would be approximately the same whether it were simply a matrix with the properties above or was provided with some securing capability by the attachment elements. An embodiment of the invention is a matrix which is capable of hydrating and acidifying the nail bed and which would be easy to use. Ease of use would be facilitated if the device had an attachment element of an adhesive backed tape or film that extended beyond the border of the matrix such that the adhesive could be used to wrap the toe or finger so as to secure the device to the affected area. Ideally the attachment element would have a relatively low moisture vapor transmission rate so as to aid in the retention of moisture in the matrix and occlude moisture loss due to evaporation. Notwithstanding any pattern that aids in application would be a desirable feature of the device. It is further contemplated that an attachment element also includes the use of an adhesive applied to the surface of the contact portion of the matrix so that the matrix would be securely fixed to the affected area by the adhesive, thereby preventing it from slipping away from the nail. An added advantage would be an open pattern adhesive since many adhesives are hydrophobic and only minimally allow moisture movement through the substrate. Such an open pattern adhesive would not interfere with the transfer of moisture and active agents from the matrix to the affected area being treated. The matrix could also comprise an attachment element of a tacky or adhesive material incorporated in the matrix so that the material could be molded to the affected area and would remain attached due to its inherent cohesive properties. These examples are not to be seen as limiting, but any attachment element that is capable of securing or maintaining the matrix at the site of application is contemplated by the present invention and many such attachment elements, for example those used for securing bandages, are known to those skilled in the art.

Examples of attachment elements include pressure sensitive adhesives including, but not limited to, polysiloxanes (e.g., polydimethyl siloxanes, polydiphenyl siloxanes, and siloxane blends), polyisobutylenes, polyacrylates, acrylic acid-acrylate copolymers (e.g., copolymers of acrylic acid copolymers with 2-ethylhexyl acrylate or isooctyl acrylate), and tacky rubbers such as polyisobutene, polybutadiene, polystyrene-isoprene copolymers, polystyrene-butadiene copolymers, and neoprene (polychloroprene).

An attachment element, such as a pressure sensitive adhesive material, with respect to highly hydrated biological tissues, such as mucosal tissue, exhibit good tack when adhered to hydrated biological substrates. To be bioadhesive, water should provide a plasticizing effect on the polymer, i.e., the polymer should be hydrophilic. For example, the range of typical adhesives includes slightly cross-linked polyacrylic and polymethacrylic acids (EP 0371 421) as well as blends of hydrophilic cellulose derivatives (40-95%) with polyethylene glycol (PEG) (U.S. Pat. No. 4,713,243). Bioadhesives become tacky as the cross linked polymer swells in significant quantities of water. Such adhesives are taught in U.S. Pat. No. 6,576,712, which is herein incorporated in its entirety.

In the present invention, it is contemplated that embodiments of compositions of the delivery platform would function on contact with the nail plate to deliver aqueous moisture that will increase the hydration level in the nail plate. The organic acid in the material would then move from the delivery platform to establish an even distribution of acidity throughout the device and the nail plate and other non-viable tissues of the nail apparatus.

A device with the above properties comprises a sheet of matrix material that could be cut to the size and shape of finger and toe nails. The material is applied directly to the nail with attachment elements provided by the tackiness of the polymer of the matrix to hold it in place and/or by attachment elements such as an adhesive polymer coating or adhesive backing securing device. Such a device is worn for several days, is preferably transparent which has cosmetic appeal, and maintains the moisture gradient due to the humectant or water retention property of the material.

Another embodiment of the composition is in the form of an amorphous hydrogel material composed of a plasticizer such as carboxymethyl cellulose or hydroxymethyl cellulose in water. Such amorphous gels are applied directly from the packaging into the application site and smeared so that they conform to the contours of the area being treated. An advantage of such a material is that it is convenient to apply, is sticky so that it localized to the area of application, and may have advantage in penetrating the lateral and proximal nail fold areas of the nail during application. Prototypes of an amorphous hydrogel were prepared so as to contain either 8, 12, or 16% w/w citric acid. Such a hydrogel is made by mixing 10% w/w glycerol into water. The appropriate amount of citric acid (8 to 16%) is then added and dissolved by stirring. 1.5% carboxymethyl cellulose and 0.3% powdered polyacrylamide matrix (for example, the matrix taught by Nangia patent or those taught in Example 1, except no glycerol or citric acid is added) was blended into the water containing citric acid and glycerol to form a viscous gel. The gels are then packed into foil laminate squeeze tubes and sealed using a bar sealer. The amorphous gels were evaluated by application of the material to infected toe nails by squeezing out sufficient material to cover the entire nail plate with a layer approximately 1-2 mm thick. The viscous gel was moderately adhesive to the nail plate so that it stayed in place regardless of whether covered with a dressing, sock or left uncovered. All of the gel samples adequately hydrated the nail plate sufficiently so as to allow debridement of the nail over the affected area without difficulty. The hydrated infected nail lifts from the nail bed and then is cut or pulled away without pain or discomfort. Subsequent applications of either the 8 or the 12% citric acid samples on a daily frequency resulted in the re-growth of healthy new nail. Prototypes containing the 16% also resulted in new nail growth but occasionally also caused mild irritation in the skin area around the affected nails.

Another embodiment of the compositions of the present invention comprise creams, salves, emulsions, lotions, pastes, white petrolatum compositions, or other lotion-type materials that provide one or more active agents. Such an embodiment would have a moisturizing effect on the keratinized layers of skin. It is thought that surrounding skin is a potent reservoir for dermatophytes that are capable of re-infecting nails. Such an embodiment hydrates the keratinized skin and create a diffusion gradient for the delivery of the active such as citric acid into the non-viable layers where the fungi would inhabit. Such embodiments are used prophylactically or actively to eliminate fungal or other microbial inhabitants of keratinized skin.

For example, the fungi commonly associated with onychomycosis are dermatophytes. This group of fungi is uniquely adapted to live in non-viable materials such as the keratinized layer of epithelium or hair. Many individuals harbor these fungi unaware of their presence. Under circumstances such as injury, supra-hydration (e.g., sweaty feet), or decrease in natural resistance, these fungi may spread to other areas. This phenomenon has been used to explain the high recurrence of infection of nail bed in individuals who have successfully resolved a bout of onychomycosis. Incorporation of organic acids, such as citric acid, in an oil and water emulsion provides a convenient delivery vehicle for application and for creating the moisture diffusion gradient in the skin sufficient to allow the migration of the active agents into the non-viable keratinized layers at the application site.

An example of such a composition is an oil emulsion. An oil emulsion containing 3% citric acid was made by dissolving citric acid powder in a commercial oil in water emulsion (Eucerin®). The blend was packaged in a cosmetic 250 g jar. The emulsion was applied daily to the feet and worked into the skin by rubbing. The material had a cooling and soothing feeling and caused no adverse effects to the skin. No new infected nails developed during the time that the cream was used.

Compositions of the present invention can also include shampoos, wherein the moisture is provided to the scalp and hair follicles or the shampoo formulation may be used as a topical cream for application of the active agents to the skin. Other compositions comprise creams or foams.

Compositions of the present invention comprise one or more active agents. Such active agents include, but are not limited to, organic acids, and antifungal agents such as selenium sulfide, resorcinol, ketoconazole (NIZORAL) Clotrimazole (such as LOTRIMIN). Terbinafine (LAMISIL), Ciclopirox olamine (LOPROX), Diflucan, anti-yeast compounds, antibacterial compounds, and antiviral compounds. Such compositions are applied topically to the site of infection or growth of the unwanted organisms.

Compounds contemplated for use in the present invention include, but are not limited to, those formulated for topical administration, for example, as a skin lotion, suntan lotion, cosmetic lotion, moisturizer, lip balm, eye makeup, face cream, and the like. A typical formulation includes one or more compounds as described herein, in combination with moisturizers, antioxidants, and the like.

Moisturizers contemplated for use in compositions include, but are not limited to, occlusive moisturizers, such as, for example, hydrocarbon oils and waxes, petroleum jelly, silicone oils, silicone derivatives, vegetable and animal fats, cocoa butter, mineral oil, fatty acids, fatty alcohols, lanolin, phospholipids, and the like; humectants, such as, for example, glycerin, honey, lactic acid, sodium lactate, ceramide, urea, propylene glycol, sorbitol, pyrrolidone carboxylic acid, glycolic acid, gelatin, vitamins, proteins, and the like; hydrophilic matrices, such as, for example, hyaluronic acid, colloidal oatmeal, and the like; essential fatty acids (e.g., Dermasil), elastin, niosomes, and the like.

Antioxidants contemplated for topical formulations include, but are not limited to, superoxide dismutase, catalase, glutathione peroxidase, glutathione reductase, gamma-tocopherol, alpha-tocopherol, ubiquinol 10, ubiquinone 10, ascorbic acid, uric acid, glutathione, and the like.

Commonly used active ingredients in sunscreen products include para-aminobenzoic acid (PABA), benzophenone, padimate O, cinnamates, homosalate, oxybenzone, octylsalicylates, and the like. Exemplary sunscreen products include SHADE SPF15 (available from Schering-Plough Corp., Memphis, Tenn.), PRE-SUN SPF15 cream (available from Westwood-Bristol Myers, Buffalo, N.Y.), SUNDOWN SPF15 (available from Proctor and Gamble, Cincinnati, Ohio), BULLFROG SPF36 (available from Chattem, Inc., Chattanooga, Tenn.), DAYLONG 16 (available from SpirigAG, CH-Egerkingen), an emulsion gel containing 70% water, ethanol, phospholipids, carbopol, sorbitol, silicone, amphisol, cetyl alcohol, tocopherol, triethanolamine, preservatives, and preparations with white petroleum jelly as vehicle, and the like.

Commonly used active ingredients in skin care products include alpha-hydroxy acids, tocopherol sorbate, ascorbate, glycolic acid, and the like.

Three alternative formulations of the topical delivery composition of the present invention as described in general terms below. These formulations are provided as examples of the present invention and are not intended to limit the invention in any way.

| Active ingredient, such as citric acid, at preferred percentage | |
|---|---|
| Formulation 1 | |
| Glycerin | 2.0% w/v |
| Propylene Glycol | 2.0% w/v |
| Dimethylisosorbide | 0.5% w/v |
| Ethanol | 35.00% v/v |
| Preservatives | as needed |
| Water | to final volume |
| Formulation 2 | |
| Glycerin | 2.40% w/v |
| Propylene Glycol | 0.60% w/v |
| Dioctyl Maleate | 1.00% w/v |
| Ethanol | 28.50% v/v |
| Preservatives | as needed |
| Water | to final volume |
| Formulation 3 | |
| Caprylic/Capric Triglyceride | 0.25% w/v |
| Propylene Glycol | 2.00% w/v |
| Dimethylisosorbide | 1.00% w/v |
| Ethanol | 40.00% w/v |
| Pantothenol | 0.25% v/v |
| Preservatives | as needed |
| UV A, B and other radiation screens | as needed |
| Free radical inhibitors or quenchers | as needed |
| Water | to final volume |

Methods of the present invention comprise treatment of dermal structures comprising applying a composition of the present invention that is effective in the prevention of growth or infection of unwanted organisms until the growth or infection by the unwanted organisms is lessened or stopped. For example, a method of treating a dermal structure comprising, a) applying a composition comprising at least one active agent to a site of a dermal condition, b) maintaining the composition at the site for a sufficient amount of time so that an effective amount of the active agent is delivered. Any of the composition taught herein can function in these methods.

Such methods may further comprise treatment of the entire host organism by the concomitant use of oral medications that aid in the prevention or cessation of the growth or infection by the unwanted organisms. Such oral treatments include antifungal pills. Antifungal pills may be taken just once (in a single dose) or may be taken once a day for 5 to 10 days, or continuously. A short period of time of dosage will mitigate against the side effects or risks usually associated with long-term use. Antifungal pills are available include Ketoconazole (NIZORAL), Fluconazole (DIFLUCAN), Griseofulvin and Itraconazole (SPORANOX).

Dermal conditions that are treated by the methods and compositions of the present invention include but are not limited to Acne, Grover's Disease, Pityriasis Lichenoides, Acanthosis Nigricans, Hair Loss (Alopecia Areata), Pityriasis, Rosea, Acrochordons, Hair Loss (Androgenic Alopecia), Pityriasis, Rubra, Pilaris, Actinic Keratosis, Hair Loss (Telogen Effluvium), Plantar Warts, Age Spots, Halo Nevus, Poison Ivy, Allergic Contact Dermatitis, Hand Dermatitis, Poison Oak, Anal Warts, Heat Rash, Pompholyx, Angioma, Herpes Simplex, Pre-cancers of the Skin, Aphthous Ulcers, Herpes Zoster (Shingles), Pruritus Ani (Itchy Butt), Athlete's Foot, Hidradenitis Suppurativa, Pseudofolliculitis Barbae, Atopic Dermatitis, Hives, Psoriasis, Atypical Moles, Hyperhidrosis, Razor Bumps, Barnacles of Aging, Ichthyosis, Rhus Allergy, Basal Cell Carcinoma, Impetigo, Rhyniophyma, Bateman's Purpura, Ingrown Hairs, Ring Worm (Body), Berloque Dermatitis, Irritant vs. Allergic Dermatitis, Ring Worm (Scalp), Boils, Jock Itch, Bruising Back of Arms, Keloids, Scabies, Bullous Pemphigoid, Keratoacanthoma, Scar, Abnormal Candida, Keratosis Pilaris, Schamberg's Disease, Carbuncles and Furuncles, Lentigines (Sun Spots), Scleroderma, Localized Cherry Angioma, Lichen Planus, Sebaceous Hyperplasia, Chiggers, Chondrodermatitis Helicis, Lichen Simplex Chronicus, Seborrheic Keratosis, Clark's Nevus, Lichen Sclerosus, Senile Angioma, Cold Sores, Lichen Striatus, Condylomata, Lupus of the Skin, Skin Aging Cysts, Lyme's Disease, Skin Tags, Dandruff, Lymphomatoid Papulosis, Solar Keratosis, Mask of Pregnancy, Squamous Cell Carcinoma, Darier's Disease, Melanoma, Stasis Dermatitis, Dermatofibroma, Melasma, Sun Burn, Diaper Dermatitis, Miliaria, Sun Damage, Discoid Lupus Erythematosus, Moles, Sun Spots, Dry Skin, Molluscum Contagiosum, Dyshidrotic Dermatitis, Mycosis Fungoides, Telogen Effluvium, Eczema, Atopic Myxoid Cysts, Tinea Capitis, Dyshidrotic, Nail Splitting, Brittle, Tinea Corporis, Nail Fungus, Tinea Cruris, Necrobiosis Lipoidica Diabeticorum, Tinea Pedis, Nickel Allergy, Tinea Versicolor, Erythema Multiforme, Nummular Dermatitis, Urticaria, Erythema Nodosum, Onychomycosis, Urticaria Pigmentosa, Folliculitis, Onychoschizia, Vitiligo, Folliculitis Keloidalis Nuchae, Perioral Dermatitis, Warts, Fordyce's Condition, Pfiesteria, Xanthomas, Granuloma Annulare, Pimples, Xerosis (Dry Skin), Pityriasis Alba, and yeast infection.

The foregoing description includes the best presently contemplated mode of carrying out the invention. This description is made for the purpose of illustrating the general principles of the inventions and should not be taken in a limiting sense. This invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

All terms used herein are considered to be interpreted in their normally acceptable usage by those skilled in the art. Patents and patent applications or references cited herein are all incorporated by reference in their entireties.

EXAMPLE 1

Formation of a Matrix Including Acrylamide

A mixing tank was charged with 161.4 kg of water and 9.1894 kg of acrylamide, 0.10347 kg of NNNN'-methylenebisacrylamide, and 9.3046 kg of glycerol were added and mixed. Then 1.0213 kg of guar gum non-gellable polysaccharide was dispersed in a mixture containing 0.9770 kg of isopropyl alcohol and 2 kg of water. The solution of guar gum was then added and dispersed into the acrylamide mixture. After suitable mixing, 0.1042 kg of TEMED was added and polymerization was catalyzed with 0.0999 kg ammonium persulphate.

While the batch was still liquid, it was poured into molds to form sheets. After gelling had occurred, sheets were transferred to a dessicator and dehydrated to form a stable intermediate stock sheet. Prior to cutting to size, the stock material was re-hydrated in a humid atmosphere. After cutting, the material was coated with petrolatum. The resulting composition was then sealed into appropriate packaging and irradiated to sterilize it.

An embodiment of the invention is a hydrogel matrix composed of a cross-linked polyacrylamide scaffolding containing ingredients that assist in the development and maintenance of an aqueous diffusion gradient in the nail plate. The matrix used in the prototypes utilized the formulation based on the Nangia patent (U.S. Pat. No. 5,196,190), such as that described above. The matrix was made by dissolving the acrylamide, bis acrylamide, guar gum, glycerol and citric acid in the aqueous charge and then initiated and catalyzed polymerization with TEMED and sodium persulfate. The resulting gel was cross linked hydrogel polymer with aqueous moisture, glycerol and citric acid. The concentration of citric acid in the formulation was approximately 6 to 16% w/w after the adjustment of the final water content to approximately 50% by weight of the matrix using a dehumidifier.

EXAMPLE 2

An alternative method for making a polyacrylamide matrix containing citric acid as the active agent was performed. The steps of Example 1 were followed, except the citric acid was not added. Once the matrix was polymerized, it was formed into the desired shape, typically a sheet approximately 25×25×0.5 cm in size. A sheet of hydrophilic matrix was created by dehydration at 45° C. resulting in approximately 3% w/w moisture. The sheet was then reconstituted with the addition of concentrated solutions of citric acid to form sheets so that the moisture content was approximately 50% by weight. The concentration of citric acid in the prototypes was 6%, 8%, 10%, 12% and 16% by weight.

The polymerized matrices with these concentrations of acid retained the normal properties of plain matrix material and were suitable for application. Sheets made by this procedure were sealed into medical grade polyethylene pouches until used.

EXAMPLE 3

The application of the sheet to infected nails was carried out by cutting the matrix to the approximate size of the nail. This was then placed onto the nail and secured using a medical grade polyurethane adhesive thin film dressing (OPSITE, Smith & Nephew). The cover dressing was applied so that the matrix parts were completely boardered on all sizes. This prevented slippage of the matrix from the nail but also occluded air contact with the matrix which might lead to dehydration. Matrix applied in this fashion could be worn for up to one week but typically were changed approximately every 2-3 days.

All prototypes, regardless of the concentration of citric acid were effective at hydrating the nail and particular the portion directly over active fungal invasion (as apparent by the white discoloration of the nail). Several individuals that volunteered to wear samples of the various strengths complained of burning sensation when the 16% sample was worn. This also occurred occasionally when the 12% sample was worn. However discontinuation resulted in relief of the sensation. Moreover individuals that experienced irritation with a higher concentration could all wear the 8% concentration without irritation.

After 1-2 applications, the portion of nail affected by fungi completely detached from the nail bed and was free floating. This detached portion could then be removed by scissors or clipper so that subsequent applications of the invention were in direct contact with the nail bed where the fungi typically reside.

Typically nail bed areas took on nearly normal appearance after about 14 days of application. Interestingly, the matrix has no apparent affect on healthy nail so that there may be no disadvantage in prolonged application where there is a high risk of re-infection from the surrounding area which often happens with people that have co-incident athletes' foot infections.

Citric acid containing matrix was used in one case of an individual with affected 7 toes (4 of the left foot and 3 on the right foot). Matrix was regularly applied every other day for 21 days to the nails of the left foot. All of the nails were hydrated within the first application. The detached nail plate substrate over the areas infected were debrided and application continued. New nail growth was observed by the $10^{th}$ day and continued until normal nail length was achieved. No changes were observed in the affected untreated nails of the right foot.

EXAMPLE 4

Skin Sensitivity

Matrices were constructed with varying amounts of citric acid, glycerol and water, as described in Examples 1 or 2. These matrices were screened for irritation and sensitization by application to the skin surface of volunteers. The prototypes and exposure results are laid out in the Table 2. CA=citric acid.

TABLE 2

Skin irritation and sensitization reactions on human volunteers.

| Prototype | Composition | Irritation Reaction (+/−) |
| --- | --- | --- |
| A.1 | Matrix containing 8% CA, 25% glycerol and 25% water. | 0/5 |
| A.2 | Matrix containing 8% CA, 15% glycerol and 50% water | 0/5 |
| A.3 | Matrix containing 12% CA, 25% glycerol and 25% water. | 1/7 |
| A.4 | Matrix containing 12% CA, 15% glycerol and 50% water. | 0/5 |
| A.5 | Matrix containing 16% CA, 25% glycerol and 25% water. | 3/5 |
| A.6 | Matrix containing 16% CA, 15% glycerol, and 50% water. | 2/4 |

The occurrence of undesirable reactions at the application sites where matrices containing 16% citric acid caused the discontinuation of investigation of materials containing this amount of acid.

EXAMPLE 5

Inhibition of Fungal Growth

Antifungal activity was determined by growth inhibition using a modified zone inhibition type assay. Strains of fungi were propagated on Sabouraud's Dextrose Agar until confluent. *Aspergillus niger* spores were harvested by rinsing culture with saline containing Tween 20. Hyphal growth from dermatophytes was also harvested using saline containing Tween 20. Hyphal growth was transferred to 15 ml sterile plastic tubes with 10 ml Tween and 3-4 glass beads. The tubes were shaken for about 2-3 minutes by hand to break up hyphae. Aliquots of 1.5 ml of hyphae or spore suspensions were dispensed to the surface of Sab-Hi agar medium (Sabouraud's containing Trypticase Soy Broth). The suspensions were spread evenly over the surface and then excess fluid was decanted and discarded. Samples of citric acid-containing, and control matrices as described in Examples 1 and 2 were prepared by punch cutting using a 5 mm bore punch. The samples were transferred to the plates and pressed to ensure contact with the plates. The plates were then incubated at 30° C. in a humidified atmosphere for 3-5 days to allow fungal growth. The plates were observed for overt appearance of zones of inhibition and then microscopically under the specimens for mycelial invasion into the contact area.

The specimens that were tested in the system were the control (FlexiGel Hydrogel Wound Dressing (plain matrix)), matrix with 8% citric acid (50% hydrated) and matrix with 12% citric acid (again 50% hydrated). The test organisms were *Trichophyton rubrum*, Epidermophyton, Microsporum, and *Aspergillus niger*. The results are provided in Table 3.

TABLE 3

Prototype action on the growth of fungi on solid agar medium.
[Diameter of Zone/Growth of fungi in contact area]

| Test Organism | FlexiGel Control | | Matrix 8% CA | | Matrix 12% CA | |
|---|---|---|---|---|---|---|
| *Aspergillus niger* | 0 mm | Heavy | 0 mm | Heavy | 0 mm | Heavy |
| *Trichophyton* | 0 mm | Heavy | 5 mm | None | 9 mm | None |
| *Epidermophyton* | 0 mm | Heavy | 2 mm | None | 4 mm | None |
| *Microsporum* | 0 mm | Heavy | 9 mm | None | 12 mm | None |

These results showed that Aspergillus was not inhibited by either of the test samples. Hyphae from this fungi grew up to, over, as well as under the citric acid containing matrices. This is not surprising since Aspergillus is commonly isolated from citrus fruits and in fact is used commercially to ferment cane sugar, molasses and dextrose into citric acid. The specimens containing citric acid inhibited all of the strains of dermatophytes. The zones of inhibition were greatest with Trichophyton and Microsporum. Continued incubation of all of the plates eventually resulted in hyphal invasion of the inhibition zones of the dermatophytes. This was likely to be due to the equilibration of citric acid into the medium resulting in a decreased concentration in the immediate vicinity of the test specimens. At the time of scanning (day 4 post inoculation) no hyphae were detected under the CA containing samples placed on the dermatophytes. By contrast, heavy hyphal growth was present under the Control sample as well as under all specimens tested on Aspergillus.

EXAMPLE 6

Transfer of Citric Acid Through Nail Plate

Effective inhibition of the dermatophytes responsible for nail infections require the penetration of the citric acid to the junction between the nail bed and the nail plate. A model of delivery was made by preparing "artificial" nail plate from bovine hoof.

Preparation of bovine hoof: Beef hoof obtained from an abitor was cleaned with soap and water and then air dried. The hoof was then mounted in a clamp device to secure it so that uniform shavings, which were small slabs of hoof, could be taken using a hand plane. The shavings were taken parallel to the surface of the face of the hoof. The shavings were collected and saved at 4° C. until required.

Transfer of acidity. The transfer of acidity from the prototypes was evaluated by placing matrix with citric acid on top of a hoof shaving which was on top of a control matrix sample. In theory, the accumulation of acid in the control matrix would only result if it passed through the hoof. To confirm this, similar set-ups were made except that a layer of polyethylene sheet was also placed between the control and test matrix to confirm that passage "through" the hoof occurred. Acid accumulation was shown by the measure of pH change, phenol red conversion, and citric acid detection (pyridine-acid anhydride test) after overnight incubation at room temperature. The results are in Table 4.

TABLE 4

Acid transfer through keratinized beef hoof simulation of nail plate.

| Sample Tested | pH | Phenol Red | Pyridine |
|---|---|---|---|
| FlexiGel Control alone | 6.5 | 2 mm | Clear |
| 12% Citric Acid alone | 3.0 | 21 mm | Dark Red |
| FlexiGel below 12% CA | 4.0 | 10 mm | Light yellow |
| FlexiGel below 12% CA separated by poly film | 6.0 | 2 mm | Clear |

The results of this study showed that protons migrate readily through the hoof to the basal layer. The migration wais not around the hoof shaving because it is blocked by a plastic impermiable barrier. The amount of citrate that was delivered to the underlying substrate is less than the amount in the delivery substrate.

EXAMPLE 7

Penetration of Acidity Through Human Nail Plate

A sample of nail clipping was taken from a volunteer as a control. The volunteer then applied the 12% CA matrix for overnight wear to a toe. The next day an additional clipping was taken from the treated toe nail. Both specimens were then oriented so that ventral aspect of each clipping was situated against the surface of a phenol red agar plate. The plate was then incubated for 2 hours at room temperature to determine if acidity penetrated through the nail plate. The untreated nail clipping showed no change in color of the surrounding phenol red whereas the treated nail clipping had an area approximately one inch in diameter surrounding it with all red cleared, indicating acidification. This simple test showed that acidity penetrated rapidly through the hydration gradient created in the nail during the treatment.

The above studies showed that the agent and delivery method are effective in the treatment of onychomycosis for the vast majority of cases since dermatophytes cause as much as 96% of the cases.

Whereas this invention has been described in detail with particular reference to its most preferred embodiments, it is understood that variations and modifications can be effected within the spirit and scope of the invention, as described herein before and as defined in the appended claims. The corresponding structures, materials, acts, and equivalents of all means plus function elements, if any, in the claims below are intended to include any structure, material, or acts for performing the functions in combination with other claimed elements as specifically claimed.

What is claimed is:

1. A method of treating a ungual condition comprising,
a) applying to an ungual structure a composition comprising: a hydrophilic polymer matrix, wherein the hydrophilic polymer matrix includes a cross-linked polyacrylamide; at least one active agent, wherein the at least one active agent comprises a citric acid present at a concentration of from about 0.1% w/w to about 16% w/w; at least one humectant, wherein the humectant is present at a concentration of from about 15% to about 25w/w, further wherein in humectant includes glycerol; a moisture management system, wherein the moisture management system includes a non-gellable polysaccharide, wherein the non-gellable polysaccharide comprises guar gum, lucerne, fenugreek, honey locust bean gum, white clover bean gum, or carob locust bean gum; a moisture content ranging from 0.1% to 50% to create a diffusion gradient from the composition to the ungual structure, wherein the hydrophilic polymer matrix directly contacts the ungual structure, wherein moisture and the at least one active agent are transferred by the diffusion gradient from the hydrophilic polymer matrix composition to the ungual structure; and an open pattern adhesive, wherein the open pattern adhesive comprises a polvsiloxane, a polyisobutylene, a polyacrylate, an acrylic acid-acrylate copolymer, a polyisobutene, a polybutadiene, a polystyrene-isoprene copolymer, a polystyrene-butadiene copolymer, a neoprene, a polyacrylic acid, a polymethacrylic acid, or a blend of a hydrophilic cellulose derivative with a polyethylene glycol; and
b) maintaining the composition at the ungual structure site for a sufficient amount of time so that an effective amount of the active agent is delivered.

2. The method of claim 1, wherein the citric acid is present at in a concentration between 4% w/w and 16% w/w.

3. An antifungal nail treatment composition comprising,
a) a solid matrix sheet comprising a hydrophilic polymer matrix, wherein the hydrophilic polymer matrix includes a cross-linked polyacrylamide;
b) at least one active antifungal agent, wherein the at least one active agent comprises a citric acid present at a concentration of from about 0.1% w/w to about 16% w/w;
c) at least one humectant, wherein the humectant is present at a concentration of from about 15% w/w to about 25% w/w, further wherein the humectant includes glycerol;
d) a moisture management system, wherein the moisture management system includes a non-gellable polysaccharide, wherein the non-gellable polysaccharide comprises guar gum, lucerne, fenugreek, honey locust bean gum, white clover bean gum, or carob locust bean gum;
e) a moisture content ranging from 0.1% to 50% to create a diffusion gradient from the composition to an ungual structure, wherein moisture and the at least one active agent are transferred from the hydrophilic polymer matrix composition to the ungual structure when the composition contacts the ungual structure; and
f) an open pattern adhesive, wherein the open pattern adhesive comprises a polysiloxane, a polyisobutylene, a polyacrylate, an acrylic acid-acrylate copolymer, a polyisobutene, a polybutadiene, a polystyrene-isoprene copolymer, a polystyrene-butadiene copolymer, a neoprene, a polyacrylic acid, a polymethacrylic acid, or a blend of a hydrophilic cellulose derivative with a polyethylene glycol.

4. The composition of claim 3, wherein the citric acid is present at in a concentration of from about 8% to about 16% w/w.

5. The composition of claim 3, wherein the composition inhibits the growth of fungi in a zone of inhibition of up to about 12 millimeters.

6. The composition of claim 5, wherein the fungi comprises trichophyton, epidermophyton, microsporum, or combinations thereof.

* * * * *